(12) United States Patent
Gimeno et al.

(10) Patent No.: US 6,399,760 B1
(45) Date of Patent: Jun. 4, 2002

(54) RP COMPOSITIONS AND THERAPEUTIC AND DIAGNOSTIC USES THEREFOR

(75) Inventors: Carlos J. Gimeno, Boston; Patrick W. Kleyn, Cambridge; Karen J. Moore, Maynard, all of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 08/697,766

(22) Filed: Aug. 29, 1996

Related U.S. Application Data

(63) Continuation of application No. 08/631,200, filed on Apr. 12, 1996, now Pat. No. 5,646,040.

(51) Int. Cl.$^7$ .................. C07H 21/04; C07H 21/02; C12P 21/06; C12N 1/20
(52) U.S. Cl. .............. 536/23.5; 536/23.1; 536/22.1; 435/69.1; 435/252.3; 435/325; 435/320.1; 435/440
(58) Field of Search .............. 536/22.1, 23.1, 536/23.5; 435/320.1, 91.1, 91.2, 252.3, 325, 365.1, 69.1, 366, 440, 441, 446, 449, 455, 463, 471, 486; 935/3, 9, 10, 22, 27, 66, 70, 71

(56) References Cited

U.S. PATENT DOCUMENTS

| | | | | |
|---|---|---|---|---|
| 4,965,188 A | * | 10/1990 | Mullis et al. | 435/6 |
| 5,646,040 A | * | 7/1997 | Kleyn et al. | 435/325 |
| 5,686,598 A | | 11/1997 | North et al. | 536/23.5 |

OTHER PUBLICATIONS

Mazzarella et al. (1994) Hum.Molec. Genet. 3(7): 1095–1101.*
Keen et al. (1995) Genomics 28: 383–388.*
Knowles et al. (1994) Hum. Molec. Genet. 3(8): 1401–1403.*
White et al. (1996) Meth. Enzymol. 266: 27–40.*
Clontech 95/96 Catalog (1995) Clonetech Laboratories, Palo Alto, CA, pp. 33–35.*
Hillier et al. (Dec. 11, 1995) disclosure of Accession No. H96925, EST database.*
Hillier et al (Nov. 29, 1995) disclosure of Accession No. H92408, EST database.*
Macke et al (May 8, 1996) disclosure of Accession No. W27507, EST database.*
Feng, Z., et al., "Characterization and Regulation of Two Testicular Inhibin/Activin βB–Subunit Messenger Ribonucleic Acids that are Transcribed from Alternate Initiation Sites," *Endocrinology*, vol. 136, No. 3, 947–955 (1995).
Kleyn, P. et al., "Identification and Characterization of the Mouse Obesity Gene Tubby: A Member of a Novel Gene Family," *Cell*, vol. 85, 281–290 (1996).
Noben–Trauth, K. et al., "A Candidate Gene for the Mouse Mutation Tubby," *Nature*, vol. 380, 534–538 (1996).
Vambutas, V. and Wolgemuth, D., "Identification and Characterization of the Developmentally Regulated Pattern of Expression in the Testis of a Mouse Gene Exhibiting Similarity to the Family of Phosphodiesterases," *Biochimica et Biophysica Acta*, vol. 1217, 203–206 (1994).
GenBank™ Accession No. D88493 for *Desulfovibrio Vulgaris DNA for Flaxodoxin*.
Copy of Genbank™ Search Using Nucleotide Sequence of rp.

* cited by examiner

Primary Examiner—Christopher S. F. Low
Assistant Examiner—Rita Mitra
(74) Attorney, Agent, or Firm—Lahive & Cockfield, LLP; Amy E. Mandragouras; Maria C. Laccotripe

(57) ABSTRACT

The present invention, which is based on the discovery of novel genes encoding rp polypeptides, features therapeutics, diagnostics and screening assays.

14 Claims, 7 Drawing Sheets

```
GAATTCCGGGAAGCTGAATGGAAGCCGGGGAGAAGTGTTGAAAGTGGAAACCCAAGCCCAGGGGAGATCCCTAGGGTGA

GGAGCCCGAGGGGGTGCGCCCAGGCTTGGGGGTAGCGGGTAGAGGCGCTGCCTCGCGGACCCGCGGATGGGACCCTGTC

TGAACCCCGCATCTCGGCTCAGCTGGGCGGAGGGGGAGGCCGCGGGAGGAGCCTTCCCCAGACCCAGCCCAGGCCCGGG

CGCCGCAGACGGTCTACGCCAGGTTCCTCAGGGACCCCGAGGCCAAGAAGCGCGACCCCCGGGAAACCTTTCTGGTAGC

CCGTGCCCCAGACGCGGAGGACGAGGAGGAGGAGGAAGAGGAGGACGAGGAGGACGAAGAAGATGAGCMGARGAAAAGA

AAGAGAAAATCCTTCTGCCTCCCAAGAARCCCCTGAGAGAGAAGAGCTCCGCAGACCTGAANGANAAGAAGGCCAANGC

CCASGGCCCAAGGGGAGACCTGGGAAGCCCTGACCCCCCACCGAAACCTCTGCGTGTTAGGAATAAGGAAGCTCCAGCA
```

```
                              M   R   K   T   K   K   K   G   S   G   E   A   D   K   D   P  16
GGGGAGGGGACCAAG              ATG AGA AAG ACC AAG AAG AAA GGG TCT GGG GAG GCC GAC AAG GAC CCC 48

S   G   S   P   A   S   A   R   K   S   P   A   A   M   F   L   V   G   E   G  36
TCA GGG AGC CCA GCC AGT GCG AGG AAG AGC CCA GCA GCC ATG TTT CTG GTT GGG GAA GGC 108

S   P   D   K   K   A   L   K   K   K   G   T   P   K   G   A   R   K   E   E  56
AGT CCT GAC AAG AAA GCC CTG AAG AAG AAA GGC ACT CCC AAA GGC GCG AGG AAG GAG GAA 168

E   E   E   E   E   A   A   T   V   T   K   N   S   N   Q   K   G   K   A   K  76
GAA GAG GAG GAG GAG GCA GCT ACG GTG ACA AAG AAC AGC AAT CAA AAG GGC AAA GCC AAA 228

G   K   G   K   K   K   A   K   E   E   R   A   P   S   P   P   V   E   V   D  96
GGA AAA GGC AAA AAG AAA GCG AAG GAG GAG AGG GCC CCG TCT CCC CCC GTG GAG GTG GAC 288

E   P   R   E   F   V   F   R   P   A   P   Q   G   R   T   V   R   C   R   L  116
GAA CCC CGG GAG TTT GTG TTC CGG CCT GCC CCC CAG GGC CGC ACG GTG CGC TGC CGG CTG 348

T   R   D   K   K   G   M   D   R   G   M   Y   P   S   Y   F   L   H   L   D  136
ACC CGG GAC AAA AAG GGC ATG GAT CGA GGC ATG TAT CCC TCC TAC TTC CTG CAC CTG GAC 408

T   E   K   K   V   F   L   L   A   G   R   K   R   K   R   S   K   T   A   N  156
ACG GAG AAG AAG GTG TTC CTC TTG GCT GGC AGG AAA CGA AAA CGG AGC AAG ACA GCC AAT 468

Y   L   I   S   I   D   P   T   N   L   S   R   G   G   E   N   F   I   G   K  176
TAC CTC ATC TCC ATC GAC CCT ACC AAT CTG TCC CGA GGA GGG GAG AAT TTC ATC GGG AAG 528

L   R   S   N   L   L   G   N   R   F   T   V   F   D   N   G   Q   N   P   Q  196
CTG AGG TCC AAC CTC CTG GGG AAC CGC TTC ACG GTC TTT GAC AAC GGG CAG AAC CCA CAG 588

R   G   Y   S   T   N   V   A   S   L   R   Q   E   L   A   A   V   I   Y   E  216
CGT GGG TAC AGC ACT AAT GTG GCA AGC CTT CGG CAG GAG CTG GCA GCT GTG ATC TAT GAA 648

T   N   V   L   G   F   R   G   P   R   R   M   T   V   I   I   P   G   M   S  236
ACC AAC GTG CTG GGC TTC CGT GGC CCC CGG CGC ATG ACC GTC ATC ATT CCT GGC ATG AGT 708

A   E   N   E   R   V   P   I   R   P   R   N   A   S   D   G   L   L   V   R  256
GCG GAG AAC GAG AGG GTC CCC ATC CGG CCC CGA AAT GCT AGT GAC GGC CTG CTG GTG CGC 768

W   Q   N   K   T   L   E   S   L   I   E   L   H   N   K   P   P   V   W   N  276
TGG CAG AAC AAG ACG CTG GAG AGC CTC ATA GAA CTG CAC AAC AAG CCA CCT GTC TGG AAC 828
```

Fig. 1A

```
     D   D   S   G   S   Y   T   L   N   F   Q   G   R   V   T   Q   A   S   V   K  296
    GAT GAC AGT GGC TCC TAC ACC CTC AAC TTC CAA GGC CGG GTC ACC CAG GCC TCA GTC AAG  888

N   F   Q   I   V   H   A   D   D   P   D   Y   I   V   L   Q   F   G   R   V  316
    AAC TTC CAG ATT GTC CAC GCT GAT GAC CCC GAC TAT ATC GTG CTG CAG TTC GGC CGC GTG  948

A   E   D   A   F   T   L   D   Y   R   Y   P   L   C   A   L   Q   A   F   A  336
    GCG GAG GAC GCC TTC ACC CTA GAC TAC CGG TAC CCG CTG TGC GCC CTG CAG GCC TTC GCC 1008

I   A   L   S   S   F   D   G   K   L   A   C   E   *                           350
    ATC GCC CTC TCC AGT TTC GAC GGG AAG CTG GCC TGC GAG TGA                          1050

CCCCAGCAGCCCCTCAGCGCCCCCAGAGCCCGTCAGCGTGGGGGAAAGGATTCAGTGGAGGCTGGCAGGGTCCCTCCAG

CAAAGCTCCCGCGGAAAACTGCTCCTGTGTCGGGGCTGACCTCTCACTGCCTCTCGGTGACCTCCGTCCTCTCCCCAGC

CTGGCACAGGCCGAGGCAGGAGGAGCCCGGACGGCGGGTAGGACGGAGATGAAGAACATCTGGAGTTGGAGCCGCACAT

CTGGTCTCGGAGCTCGCCTGCGCCGCTGTGCCCCCCTCCTCCCCGCGCCCCAGTCACTTCCTGTCCGGGAGCAGTAGTC

AGTGTTGTTTTAACCTCCCCTCTCCCCGGGACCGCGCTAGGGCTCCGAGGAGCTGGGGCGGGCTAGGAGGAGGGGGTAG

GTGATGGGGGACGAGGGCCAGGCACCCACATCCCCAATAAAGCCGCGTCCTTGGCMAAAAAAAAAAAAAAAAAAAAAAA

AAAAAAAAAAAAAAAAAAAAAAAAAAAAAAAAAAAAAAAAAAAAAAAAAAAAAAAAAAAAAAAAAAAAAAAAAAAAAAA

AAAACCGGAATTC
```

Fig. 1B

```
  V   I   K   N   S   N   Q   K   G   K   A   K   G   K   G   K   K   K   A   K    20
GTG ATA AAG AAC AGC AAT CAA AAG GGC AAA GCC AAA GGA AAA GGC AAA AAG AAA GCG AAG    60

E   E   R   A   P   S   P   P   V   E   V   D   E   P   R   E   F   V   L   R    40
GAG GAG AGG GCC CCG TCT CCC CCC GTG GAG GTG GAC GAA CCC CGG GAG TTT GTG CTC CGG   120

P   A   P   Q   G   R   T   V   R   C   R   L   T   R   D   K   K   G   M   D    60
CCT GCC CCC CAG GGC CGC ACG GTG CGC TGC CGG CTG ACC CGG GAC AAA AAG GGC ATG GAT   180

R   G   M   Y   P   S   Y   F   L   H   L   D   T   E   K   K   V   F   L   L    80
CGA GGC ATG TAT CCC TCC TAC TTC CTG CAC CTG GAC ACG GAG AAG AAG GTG TTC CTC TTG   240

A   G   R   K   R   K   R   S   K   T   A   N   Y   L   I   S   I   D   P   T   100
GCT GGC AGG AAA CGA AAA CGG AGC AAG ACA GCC AAT TAC CTC ATC TCC ATC GAC CCT ACC   300

N   L   S   R   G   G   E   N   F   I   G   K   L   R   S   N   L   L   G   N   120
AAT CTG TCC CGA GGA GGG GAG AAT TTC ATC GGG AAG CTG AGG TCC AAC CTC CTG GGG AAC   360

R   F   T   V   F   D   N   G   Q   N   P   Q   R   G   Y   S   T   N   V   A   140
CGC TTC ACG GTC TTT GAC AAC GGG CAG AAC CCA CAG CGT GGG TAC AGC ACT AAT GTG GCA   420

S   L   R   Q   E   L   A   A   V   I   Y   E   T   N   V   L   G   F   R   G   160
AGC CTT CGG CAG GAG CTG GCA GCT GTG ATC TAT GAA ACC AAC GTG CTG GGC TTC CGT GGC   480

P   R   R   M   T   V   I   I   P   G   M   S   A   E   N   E   R   V   P   I   180
CCC CGG CGC ATG ACC GTC ATC ATT CCT GGC ATG AGT GCG GAG AAC GAG AGG GTC CCC ATC   540

R   P   R   N   A   S   D   G   L   L   V   R   W   Q   N   K   T   L   E   S   200
CGG CCC CGA AAT GCT AGT GAC GGC CTG CTG GTG CGC TGG CAG AAC AAG ACG CTG GAG AGC   600

L   I   E   L   H   N   K   P   P   V   W   N   D   D   S   G   S   Y   T   L   220
CTC ATA GAA CTG CAC AAC AAG CCA CCT GTC TGG AAC GAT GAC AGT GGC TCC TAC ACC CTC   660

N   F   Q   G   R   V   T   Q   A   S   V   K   N   F   Q   I   V   H   A   D   240
AAC TTC CAA GGC CGG GTC ACC CAG GCC TCA GTC AAG AAC TTC CAG ATT GTC CAC GCT GAT   720

D   P   D   Y   I   V   L   Q   F   G   R   V   A   E   D   A   F   T   L   D   260
GAC CCC GAC TAT ATC GTG CTG CAG TTC GGC CGC GTG GCG GAG GAC GCC TTC ACC CTA GAC   780

Y   R   Y   P   L   C   A   L   Q   A   F   A   I   A   L   S   S   F   D   G   280
TAC CGG TAC CCG CTG TGC GCC CTG CAG GCC TTC GCC ATC GCC CTC TCC AGT TTC GAC GGG   840

K   L   A   C   E   *                                                            285
AAG CTG GCC TGC GAG TGA CCCCAGCAGCCCCTCAGCGCCCCCAGAGCCCGTCAGCGTGGG                 900

GGAAAGGATTCAGTGGAGGCTGGCAGGGTCCCTCCAGCAAAGCTCCCGCGGAAAACTGCT                       960

CCTGTGTCGGGGCTGACCTCTCACTGCCTCTCGGTGACCTCCGTCCTCTCCCCAGCCTGG                      1020

CACAGGCCGAGGCAGGAGGAGCCCGGACGGCGGGTAGGACGGAGATGAAGAACATCTGGA                      1080

GTTGGAGCCGCACATCTGGTCTCGGAGCTCGCCTGCGCCGCTGTGCCCCCCTCCTCCCCG                      1140

CGCCCCAGTCACTTCCTGTCCGGGAGCAGTAGTCATTGTTGTTTTAACCTCCCCTCTCCC                      1200

CGGGACCGCGCTAGGGCTCCGAGGAGCTGGGGCGGGCTAGGAGGAGGGGGTAGGTGATGG                      1260

GGGACGAGGGCCAGGCACCCACATCCCCAATAAAGCCGCGTCCTTGGCAAAAAAAAAAAA                      1320

AAAAAAAAAAAAAAAAAA                                                                1338
```

Fig. 2

```
                                                          CTGCAGGATTCGGCACGAGCAGCGGTCGGGCCGGGG
AGGATGCGGCCCGGGGCGGCCCGAGAGTTGAGCAGGGTCCCCGCGCCAGCCCCGAGCGGTCCCGGCCAQCGGAGCCGCA
                          M   T   S   K   P   H   S   D   W   I   P   Y   S   V     14
GCCGCCGCCCCGCCCCGGGAGA ATG ACT TCC AAG CCG CAT TCC GAC TGG ATT CCT TAC AGT GTC     42

L   D   D   E   G   S   N   L   R   Q   Q   K   L   D   R   Q   R   A   L   L      34
CTA GAT GAT GAG GGC AGC AAC CTG AGG CAG CAG AAG CTC GAC CGG CAG CGG GCC CTG TTG    102

E   Q   K   Q   K   K   K   R   Q   E   P   L   M   V   Q   A   N   A   D   G      54
GAA CAG AAG CAG AAG AAG AAG CGC CCA GAG CCC TTG ATG GTA CAG GCC AAT GCA GAT GGA    162

R   P   R   S   R   R   A   R   Q   S   E   E   Q   A   P   L   V   E   S   Y      74
CGG CCC CGG AGT CGG CGA GCC CGG CAG TCA GAG GAG CAA GCC CCC CTG GTG GAG TCC TAC    222

L   S   S   S   G   S   T   S   Y   Q   V   Q   E   A   D   S   I   A   S   V      94
CTC AGC AGC AGT GGC AGC ACC AGC TAC CAA GTT CAA GAG GCC GAC TCG ATT GCC AGT GTA    282

Q   L   G   A   T   R   P   P   A   P   A   S   A   K   K   S   K   G   A   A     114
CAG CTG GGA GCC ACC CGC CCA CCA GCA CCA GCT TCA GCC AAG AAA TCC AAG GGA GCG GCT    342

A   S   G   G   Q   G   G   A   P   R   K   E   K   K   G   K   H   K   G   T     134
GCA TCT GGG GGC CAG GGT GGA GCC CCT AGG AAG GAG AAG AAG GGA AAG CAT AAA GGC ACC    402

S   G   P   A   T   L   A   E   D   K   S   E   A   Q   G   P   V   Q   I   L     154
AGC GGG CCA GCA ACT CTG GCA GAA GAC AAG TCT GAG GCC CAA GGC CCA GTG CAG ATC TTG    462

T   V   G   Q   S   D   H   D   K   D   A   G   E   T   A   A   G   G   G   A     174
ACT GTG GGA CAG TCA GAC CAC GAC AAG GAT GCG GGA GAG ACA GCA GCC GGC GGG GGC GCA    522

Q   P   S   G   Q   D   L   R   A   T   M   Q   R   K   G   I   S   S   S   M     194
CAG CCC AGT GGG CAG GAC CTC CGT GCC ACG ATG CAG AGG AAG GGC ATC TCC AGC AGC ATG    582

S   F   D   E   D   E   D   E   D   E   N   S   S   S   S   S   Q   L   N   S     214
AGC TTT GAC GAG GAC GAG GAT GAG GAT GAA AAC AGC TCC AGC TCC TCC CAG CTA AAC AGC    642

N   T   R   P   S   S   A   T   S   R   K   S   I   R   E   A   A   S   A   P     234
AAC ACC CGC CCT AGT TCT GCC ACT AGC AGA AAG TCC ATC CGG GAG GCA GCT TCA GCC CCC    702

S   P   A   A   P   E   P   P   V   D   I   E   V   Q   D   L   E   E   F   A     254
AGC CCA GCC GCC CCA GAG CCA CCA GTG GAT ATT GAG GTC CAG GAT CTA GAG GAG TTT GCA    762

L   R   P   A   P   Q   G   I   T   I   K   C   R   I   T   R   D   K   K   G     274
CTG AGG CCA GCC CCA CAA GGG ATC ACC ATC AAA TGC CGC ATC ACT CGG GAC AAG AAG GGG    822

M   D   R   G   M   Y   P   T   Y   F   L   H   L   D   R   E   D   G   K   K     294
ATG GAC CGC GGC ATG TAC CCC ACC TAC TTT CTG CAC CTA GAC CGT GAG GAT GGC AAG AAG    882

V   F   L   L   A   G   R   K   R   K   K   S   K   T   S   N   Y   L   I   S     314
GTG TTC CTC CTG GCG GGC AGG AAG AGA AAG AAG AGT AAA ACT TCC AAT TAC CTC ATC TCT    942

V   D   P   T   D   L   S   R   G   G   D   S   Y   I   G   K   L   R   S   N     334
GTG GAC CCA ACA GAC TTG TCT CGG GGA GGC GAT AGC TAT ATC GGG AAA TTG CGG TCC AAC   1002

L   M   G   T   K   F   T   V   Y   D   N   G   V   N   P   Q   K   A   S   S     354
CTG ATG GGC ACC AAG TTC ACC GTT TAT GAC AAT GGC GTC AAC CCT CAG AAG GCA TCC TCT   1062
```

Fig. 3A

```
  S   T   L   E   S   G   T   L   R   Q   E   L   A   A   V   C   Y   E   T   N    374
TCC ACG CTG GAA AGC GGA ACC TTG CGC CAG GAG CTG GCA GCG GTG TGC TAT GAG ACA AAT   1122

V   L   G   F   K   G   P   R   K   M   S   V   I   V   P   G   M   N   M   V    394
GTC CTA GGC TTC AAG GGA CCT CGG AAG ATG AGT GTG ATC GTC CCA GGC ATG AAC ATG GTT   1182

H   E   R   V   C   I   R   P   R   N   E   H   E   T   L   L   A   R   W   Q    414
CAT GAG AGA GTC TGT ATC CGC CCC CGC AAT GAA CAT GAG ACC CTG TTA GCA CGC TGG CAG   1242

N   K   N   T   E   S   I   I   E   L   Q   N   K   T   P   V   W   N   D   D    434
AAC AAG AAC ACG GAG AGC ATC ATT GAG CTG CAG AAC AAG ACG CCA GTC TGG AAT GAT GAC   1302

T   Q   S   Y   V   L   N   F   K   G   R   V   T   Q   A   S   V   K   N   F    454
ACA CAG TCC TAT GTA CTT AAC TTC AAG GGC CGT GTC ACA CAG GCT TCT GTG AAG AAC TTC   1362

Q   I   I   H   G   N   D   P   D   Y   I   V   M   Q   F   G   R   V   A   E    474
CAG ATC ATC CAC GGC AAT GAC CCG GAC TAC ATC GTC ATG CAG TTT GGC CGG GTA GCA GAA   1422

D   V   F   T   M   D   Y   N   Y   P   L   C   A   L   Q   A   F   A   I   A    494
GAT GTG TTC ACC ATG GAT TAC AAC TAC CCA CTG TGT GCA CTG CAG GCC TTC GCC ATT GCT   1482

L   S   S   F   D   S   K   L   A   C   *                                         505
CTG TCC AGC TTT GAC AGC AAG CTG GCC TGC GAG TAG AGGCCCCCCACTGCCGTTAGGTGGCCCAGTC   1515

CGGAGTGGAGCTTGCCTGCCTGCCAAGACAGGCCTGCCTACCCTCTGTTCATAGGCCCTCTATGGGCTTTCTGGTCTGA

CCAACCAGAGATTGGTTTGCTCTGCCTCTGCTGCTTGA
```

Fig. 3B

```
                                                    TGGCGTGCAGCAGGGGCCTCGGCGGGGCCC
AGCCCNCCGGTCCCGGGGAGGATACGTCCCGGGGGCGGCCCGGGAGCTGAGCAGGCCCCCCGCGCCGGCCCCTCCGGGC
                                             M   T   S   K   P   H   S   D   W      9
CCCGGCCTCCAGAGCCGCAGCCACCGCCCCGCCCCCGAGAGAC ATG ACT TCC AAG CCG CAT TCC GAC TGG   27

I   P   Y   S   V   L   D   D   E   G   R   N   L   R   Q   Q   K   L   D   R    29
 ATT CCC TAC AGT GTC TTA GAT GAT GAG GGC AGA AAC CTG AGG CAG CAG AAG CTT GAT CGG   87

Q   R   A   L   L   E   Q   K   Q   K   K   K   R   Q   E   P   L   M   V   Q    49
 CAG CGG GCC CTG CTG GAG CAG AAG CAG AAG AAG AAG CGC CAG GAG CCC CTG ATG GTG CAG  147

A   N   A   D   G   R   P   R   S   R   R   A   R   Q   S   E   E   Q   A   P    69
 GCC AAT GCA GAT GGG CGG CCC CGG AGC CGG CGG GCC CGG CAG TCA GAG GAA CAA GCC CCC  207

L   V   E   S   Y   L   S   S   S   G   S   T   S   Y   Q   V   Q   E   A   D    89
 CTG GTG GAG TCC TAC CTC AGC AGC AGT GGC AGC ACC AGC TAC CAA GTT CAA GAG GCC GAC  267

S   L   A   S   V   Q   L   G   A   T   R   P   T   A   P   A   S   A   K   R   109
 TCA CTC GCC AGT GTG CAG CTG GGA GCC ACG CGC CCA ACA GCA CCA GCT TCA GCC AAG AGA  327

T   K   A   A   A   T   A   G   G   Q   G   G   A   A   R   K   E   K   K   G   129
 ACC AAG GCG GCA GCT ACA GCA GGG GGC CAG GGT GGC GCC GCT AGG AAG GAG AAG AAG GGA  387

K   H   K   G   T   S   G   P   A   A   L   A   E   D   K   S   E   A   Q   G   149
 AAG CAC AAA GGC ACC AGC GGG CCA GCA GCA CTG GCA GAA GAC AAG TCT GAG GCC CAA GGC  447

P   V   Q   I   L   T   V   G   Q   S   D   H   A   Q   D   A   G   E   T   A   169
 CCA GTG CAG ATT CTG ACT GTG GGC CAG TCA GAC CAC GCC CAG GAC GCA GGG GAG ACG GCA  507

A   G   G   E   R   P   S   G   Q   D   L   R   A   T   M   Q   R   K   G       189
 GCT GGT GGG GGC GAA CGG CCC AGC GGG CAG GAT CTC CGT GCC ACG ATG CAG AGG AAG GGC  567

I   S   S   S   M   S   F   D   E   D   E   E   D   E   E   E   N   S   S   S   209
 ATC TCC AGC AGC ATG AGC TTT GAC GAG GAT GAG GAG GAT GAG GAG GAG AAT AGC TCC AGC  627

S   S   Q   L   N   S   N   T   R   P   S   S   A   T   S   R   K   S   V   R   229
 TCC TCC CAG CTA AAT AGT AAC ACC CGC CCC AGC TCT GCT ACT AGC AGG AAG TCC GTC AGG  687

E   A   A   S   A   P   S   P   T   A   P   E   Q   P   V   D   V   E   V   Q   249
 GAG GCA GCC TCA GCC CCT AGC CCA ACA GCT CCA GAG CAA CCA GTG GAC GTT GAG GTC CAG  747

D   L   E   E   F   A   L   R   P   A   P   Q   G   I   T   I   K   C   R   I   269
 GAT CTT GAG GAG TTT GCA CTG AGG CCG GCC CCC CAG GGT ATC ACC ATC AAA TGC CGC ATC  807

T   R   D   K   K   G   M   D   R   G   M   Y   P   T   Y   F   L   H   L   D   289
 ACT CGG GAC AAG AAA GGG ATG GAC CGG GGC ATG TAC CCC ACC TAC TTT CTG CAC CTG GAC  867

R   E   D   G   K   K   V   F   L   L   A   G   R   K   R   K   K   S   K   T   309
 CGT GAG GAT GGG AAG AAG GTG TTC CTC CTG GCG GGA AGG AAG AGA AAG AAG AGT AAA ACT  927

S   N   Y   L   I   S   V   D   P   T   D   L   S   R   G   G   D   S   Y   I   329
 TCC AAT TAC CTC ATC TCT GTG GAC CCA ACA GAC TTG TCT CGA GGA GGG GAC AGC TAT ATC  987

G   K   L   R   S   N   L   M   G   T   K   F   T   V   Y   D   N   G   V   N   349
 GGG AAA CTG CGG TCC AAC TTG ATG GGC ACC AAG TTC ACT GTT TAT GAC AAT GGA GTC AAC 1047
```

Fig. 4A

```
P   Q   K   A   S   S   S   T   L   E   S   G   T   L   R   Q   E   L   A   A    369
CCT CAG AAG GCC TCA TCC TCC ACT TTG GAA AGT GGA ACC TTA CGT CAG GAG CTG GCA GCT  1107

V   C   Y   E   T   N   V   L   G   F   K   G   P   R   K   M   S   V   I   V    389
GTG TGC TAC GAG ACA AAC GTC TTA GGC TTC AAG GGG CCT CGG AAG ATG AGC GTG ATT GTC  1167

P   G   M   N   M   V   H   E   R   V   S   I   R   P   R   N   E   H   E   T    409
CCA GGC ATG AAC ATG GTT CAT GAG AGA GTC TCT ATC CGC CCC CGC AAC GAG CAT GAG ACA  1227

L   L   A   R   W   Q   N   K   N   T   E   S   I   I   E   L   Q   N   K   T    429
CTG CTA GCA CGC TGG CAG AAT AAG AAC ACG GAG AGT ATC ATC GAG CTG CAA AAC AAG ACA  1287

P   V   W   N   D   D   T   Q   S   Y   V   L   N   F   H   G   R   V   T   Q    449
CCT GTC TGG AAT GAT GAC ACA CAG TCC TAT GTA CTC AAC TTC CAT GGG CGC GTC ACA CAG  1347

A   S   V   K   N   F   Q   I   I   H   G   N   D   P   D   Y   I   V   M   Q    469
GCC TCC GTG AAG AAC TTC CAG ATC ATC CAT GGC AAT GAC CCG GAC TAC ATC GTG ATG CAG  1407

F   G   R   V   A   E   D   V   F   T   M   D   Y   N   Y   P   L   C   A   L    489
TTT GGC CGG GTA GCA GAG GAT GTG TTC ACC ATG GAT TAC AAC TAC CCG CTG TGT GCA CTG  1467

Q   A   F   A   I   A   L   S   S   F   D   S   K   L   A   C   E   *            506
CAG GCC TTT GCC ATT GCC CTG TCC AGC TTC GAC AGC AAG CTG GCG TGC GAG TAG AGGCCTC  1528

TTCGTGCCCTTTGGGGTTGCCCAGCCTGGAGCGGAGCTTGCCTGCCTGCCTGTGGAGACAGCCCTGCCTATCCTCTGTA  1607

TATAGGCCTTCCGCCAGATGAAGCTTTGGCCCTCAGTGGGCTCCCTGGCCCAGCCAGCCAGGAACTGGCTCCTTTGGCT  1686

CTGCTACTGAGGCAGGGGAGTAGTGGAGAGCGGGTGGGTGGGTGTTGAAGGGATTGAGAATTAATTCTTTCCATGCCAC  1765

GAGGATCAACACACACTCCCACCCTTGGGTAGTAAGTGGTTGTTGTNAGTCGGTACTTTACCAAAGCTTGAGCAACCTC  1844

TTCCAAGCTTGGGAAAGGGCCGCAAAAAGGCATTAGGAGGGGAG                                    1888
```

Fig. 4B

US 6,399,760 B1

RP COMPOSITIONS AND THERAPEUTIC AND DIAGNOSTIC USES THEREFOR

This application is a continuation, which claims priority of Application Ser. No. 08/631200 filed on Apr. 12, 1996 now U.S. Pat. No. 5,646,040.

BACKGROUND OF THE INVENTION

Retinitis pigmentosa (RP) is a group of human hereditary retinal degenerations characterized by night blindness and loss of peripheral vision. RP sometimes progresses to total blindness. Cardinal clinical features of RP include retinal pigmentary disturbances, attenuation of the retinal vasculature, a waxy pale appearance of the optic nerve head, and abnormalities of retinal function. RP is the most common mendelian degenerative retinal disorder, affecting 1.5 million individuals worldwide (Kumar Singh, R., Farrar, G. J., Mansergh, F., Kenna, P., Bhattacharya, S., Gal, A. and Humphries, P. (1993) *Hum. Mol. Genet.* 2, 875–878). Among Caucasians in the United States, when not associated with other abnormalities, RP is inherited most frequently as an autosomal recessive (84% of cases), next as an autosomal dominant (10%), and least frequently as an X-linked recessive disorder (6%) (Boughman, J. A., Conneally, P. M. and Nance, W. E. (1980) *Am. J Hum. Genet.* 32, 223–235).

Significant nonallelic heterogeneity has been found in autosomal dominant RP (adRP) and in X-linked RP. For adRP, mutations in the rhodopsin gene on 3q (Sung, c. H., Davenport, C. M., Hennessey, J. C., Maumenee, I. H., Jacobson, S. G., Heckenlively, J. R., Nowakowski, R., Fishmanm, G., Gouras, P. and Nathan, J. (1991) *Proc. Natl. Acad. Sci. USA* 88, 6481–6485; Ingleheam, C. F., Keen, T. J., Bashir, R., Jay, M., Fitzke, F., Bird, A. C., Crombie, A. and Bhattacharya, S. (1992) *Hum. Mol. Genet.* 1, 41–45; Humphries, P., Kenna, P. and Farrar, G. J. (1992) *Science* 256, 804–808), and the peripherin gene on 6p have been found (Farrar, G. J., Kenna, P., Jordan, S. A., Kumar Singh, R., Humphries, M. M., Sharp, E. M., Sheils, d. M. and Humphries, P. (1991) *Nature* 354, 478–480; Kajiwara, K., Hah, L. B., Mukai, S., Travis, G. H., Berson, E. L. and Dryja, T. P. (1991) *Nature* 354, 480–483; Farrar, G. J., Kenna, P., Jordan, S. A., Kumar Singh, R., Humphries, M. M., Sharp, E. M., Sheils, D. and Humphries, P. (1993) *Genomics* 15, 466). In addition, genetic linkage of adRP is observed to loci on chromosomes 8 (Blanton, S. H., Heckenlively, J. R., Cottingham, A. W., Friedman, J., Sadler, L. A., Wagner, M., Friedman, L. H. and Daiger, S. P. (1991) *Genomics* 11, 857–869), 7p (Ingleheam, C. F., Carter, S. A., Keen, T. J., Lindsey, J., Stephenson, A. M., Bashir, R., al Maghtheh, M., Moore, A. T., Jay, M., Bird, A. C. and Bhattacharya, S. S. (1993) *Nature Genet.* 4, 51–53), 7q (Jordan, S. A., Farrar, G. J., Kenna, P., Humphries, M. M., Sheils, D. M., Kumar Singh, R., Sharp, E. M., Soriano, N., Ayuso, C., Benitez, J. and et al, (1993) *Nature Genet.* 4, 130–134), and 19 (Al-Maghtheh, M., Inglehearn, C. F., Keen, T. J., Evans, K., Moore, A. T., Jay, M., Bird, A. C. and Bhattacharya, S. S. (1994) *Hum. Mol. Genet.* 3, 351–354). For the X-linked form of the disorder, two loci have been implicated (Ott, J., Bhattacharya, S., Chen, J. D., Denton, M. J., Donald, J., Dubay, C., Farrar, G. J., Fishman, G. A., Frey, D., Gal, A., Humphries, P., Jay, B., Jay, M., Litt, M., Machler, M., Musarella, M., Neugebauer, M., Nussbaum, R. L., Terwilliger, J. D., Weleber, R. G., Wirth, B., Wong, F., Worton, R. G. and Wright, A. F. (1990) *Proc. Natl. Acad. Sci. USA* 87, 701–704). Genetic linkage has not been reported for autosomal recessive RP (arRP), but mutations that cosegregate with arRP have been found in the β-subunit of rod phosphodiesterase on chromosome 4p (McLaughlin, M. E., Sandberg, M. A., Berson, E. L. and Dryja, T. P. (1993) *Nature Genet.* 4, 130–134), rhodopsin (Rosenfeld, P. J., Cowley, G. S., McGee, T. L., Sandberg, M. A., Berson, E. L. and Dryja, T. P. (1992) *Nature Genet.* 1, 209–213), and possibly the rod cGMP-gated channel gene (McGee, T. L., Lin, D., Berson, E. L. and Dryja, T. P. (1994) *Invest. Ophthalmol. Vis. Sci.* (Suppl.) 35, 1716 (Abstract)). The regions around rhodopsin and peripherin have been excluded as a cause of arRP in a large Dutch pedigree (Bleeker Wagemakers, L. M., Gal, A., Kumar Singh, R., Ingeborgh van den Born, L., Li, Y., Schwinger, E., Sandkuijl, L. A., Bergen, A. A., Kenna, P., Humphries, P. and Farrar, G. J. (1992) *Genomics* 14, 811–812), suggesting that the recessive form of the disorder is also genetically heterogeneous.

A locus for autosomal recessive retinitis pigmentosa has been mapped on chromosome 6p by linkage analysis (Knowles, J. A., et. al., (1994) *Hum. Mol. Genet.* 3:1401–1403). This locus is approximately 20 centimorgans telomeric from the previously described adRP disease gene, peripherin, and thus represents a novel disease locus. The approximate 95% confidence interval for arRP spanning the D6S291 locus is 8.5% centimorgans. This interval of chromosome 6p contains the HLA complex. HLA associations have been found in several human uveitic diseases (Nussenblatt, R. B. et al., (1989) *Uveitis: Fundamentals and Clinical Practice: Year Book Medical Publishers*), and the 1-A subregion of the H-2 complex in a mouse model of autoimmune uveoretinitis (Caspi, R. R., et. al., (1992), *Curr. Eye Res.* 11 (Suppl.) 81–86; Caspi, R. R., et, al., (1992) *J. Immunol.*, 148:2384–2389).

2. SUMMARY OF THE INVENTION

The present invention is based on the discovery of novel molecules, referred to herein as rp nucleic acid and polypeptide molecules. Exemplary rp molecules, the first containing a Bac clone genomic DNA and the second containing the cDNA shown in FIGS. 1A-1B have been deposited with the American Type Culture Collection (ATCC) and have been assigned ATCC designation numbers: 98144 (deposited Aug. 22, 1996) and 98147 (deposited Aug. 23, 1996), respectively.

The human rp gene (FIG. 1), which is approximately 1050 nucleotides in length, is predominantly expressed in the retina, consistent with the phenotypic abnormalities seen in Retinitis Pigmentosa patients. In addition, the gene was found to map very close (2.8 cR or about 1 Mb) to marker D6S291 on chromosome 6. This marker is the most tightly linked marker to the RP14 retinitis pigmentosa locus. The human rp gene encodes a 349 amino acid protein, that weighs approximately 38880 daltons.

The human rp gene is 56.4% identical to the human tub gene; and the hrp protein is 46% identical to htub. Although the N-terminus of the two gene products are dissimilar, the most conserved region of the two gene products are 66.4% identical. Accordingly and as discussed further herein, the tub and rp genes may perform similar molecular functions in different biochemical pathways or may even function in the same biochemical pathway(s).

In one aspect, the invention features isolated vertebrate rp nucleic acid molecules. The disclosed molecules can be non-coding, (e.g. probe, antisense or ribozyme molecules) or can encode a functional rp polypeptide (e.g. a polypeptide which specifically modulates, e.g., by acting as either an agonist or antagonist, at least one bioactivity of the human rp polypeptide). In one embodiment, the nucleic acid molecules hybridize to the rp gene contained in ATCC Designation Nos. 98144 or 98147 or to the complement of the rp gene contained in ATCC Designation Nos. 98144 or 98147. In another embodiment, the nucleic acids of the present invention can hybridize to a vertebrate rp gene or to the complement of a vertebrate rp gene. In a further embodiment, the claimed nucleic acid hybridizes with the coding sequence designated in at least one of SEQ ID Nos: 1 or 3 or to the complement to the coding sequence designated in at least one of SEQ ID Nos: 1 or 3. In a preferred embodiment, the hybridization is conducted under mildly stringent or stringent conditions.

In further embodiments, the nucleic acid molecule is a rp nucleic acid that is at least 70%, preferably 80%, more preferably 85%, and even more preferably at least 95% homologous in sequence to the nucleic acids shown as SEQ ID Nos: 1 or 3 or to the complement of the nucleic acids shown as SEQ ID Nos: 1 or 3. In another embodiment, the rp nucleic acid molecule encodes a polypeptide that is at least 90% and more preferably at least 94% similar in sequence to the polypeptide shown in SEQ ID No: 2. In a further embodiment, the nucleic acid molecule is a rp nucleic acid that is at least 70%, preferably 80%, more preferably 85% and even more preferably at least 90% or 95% similar in sequence to the rp gene contained in ATCC Designation Nos. 98144 or 98147.

The invention also provides probes and primers comprising substantially purified, oligonucleotides, which correspond to a region of nucleotide sequence which hybridizes to at least 6 consecutive nucleotides of the sequences set forth as SEQ ID Nos: 1 or 3 or complements of the sequences set forth as SEQ ID Nos: 1 or 3, or naturally occurring mutants thereof. In preferred embodiments, the probe/primer further includes a label group attached thereto, which is capable of being detected.

For expression, the subject rp nucleic acids can include a transcriptional regulatory sequence, e.g. at least one of a transcriptional promoter (e.g., for constitutive expression or inducible expression) or transcriptional enhancer sequence, which regulatory sequence is operably linked to the rp gene sequence. Such regulatory sequences in conjunction with a rp nucleic acid molecule can be useful vectors for gene expression. This invention also describes host cells transfected with said expression vector whether prokaryotic or eukaryotic and in vitro (e.g. cell culture) and in vivo (e.g. transgenic) methods for producing rp proteins by employing said expression vectors.

In another aspect, the invention features isolated rp polypeptides, preferably substantially pure preparations e.g. of plasma purified or recombinantly produced rp polypeptides. In one embodiment, the polypeptide is identical to or similar to a rp protein represented in SEQ ID No: 2. Related members of the vertebrate and particularly the mammalian rp family are also within the scope of the invention. Preferably, a rp polypeptide has an amino acid sequence at least 66.5% homologous and preferably at least 70, 80, 85, 90 or 95% homologous to the polypeptide represented in SEQ ID No: 2. In a preferred embodiment, the rp polypeptide that is encoded by a nucleic acid which hybridizes with a nucleic acid sequence represented in one of SEQ ID Nos: 1 or 3 or with the gene or gene fragment contained in ATCC Designation Nos. 98144 or 98147. The subject rp proteins also include modified protein, which are resistant to post-translation modification, as for example, due to mutations which alter modification sites (such as tyrosine, threonine, serine or aspargine residues), or which prevent glycosylation of the protein, or which prevent interaction of the protein with intracellular proteins involved in signal transduction.

The rp polypeptide can comprise a full length protein, such as represented in SEQ ID No: 2, or it can comprise a fragment corresponding to one or more particular motifs/domains, or to arbitrary sizes, e.g., at least 5, 10, 25, 50, 100, 150, 175, 200, 225, 250,275, 300, 325, 330, 335 or 340 amino acids in length. A particularly preferred rp polypeptide is comprise of 349 amino acids and has a molecular weight of about 38880 daltons.

Another aspect of the invention features chimeric molecules (e.g. fusion proteins) comprised of a rp protein. For instance, the rp protein can be provided as a recombinant fusion protein which includes a second polypeptide portion, e.g., a second polypeptide having an amino acid sequence unrelated (heterologous) to the rp polypeptide (e.g. the second polypeptide portion is glutathione-S-transferase, an enzymatic activity such as alkaline phosphatase or an epitope tag).

Yet another aspect of the present invention concerns an immunogen comprising a rp polypeptide in an immunogenic preparation, the immunogen being capable of eliciting an immune response specific for a rp polypeptide; e.g. a humoral response, an antibody response and/or cellular response. In preferred embodiments, the immunogen comprises an antigenic determinant, e.g. a unique determinant, from the protein represented in SEQ ID No: 2.

A still further aspect of the present invention features antibodies and antibody preparations specifically reactive with an epitope of the rp protein. In preferred embodiments the antibody specifically binds to at least one epitope represented in SEQ ID No: 2.

The invention also features transgenic non-human animals which include (and preferably express) a heterologous form of a rp gene described herein, or which misexpress an endogenous rp gene (e.g., an animal in which expression of one or more of the subject rp proteins is disrupted). Such a transgenic animal can serve as an animal model for studying cellular and tissue disorders comprising mutated or misexpressed rp alleles or for use in drug screening. Alternatively, such a transgenic animal can be useful for expressing recombinant rp polypeptides.

In yet another aspect, the invention provides assays, e.g., for screening test compounds to identify inhibitors, or alternatively, potentiators, of an interaction between a rp protein and, for example, a virus, an extracellular ligand of the rp protein, or an intracellular protein which binds to the rp protein. An exemplary method includes the steps of (i) combining a rp polypeptide or bioactive fragments thereof, a rp target molecule (such as a rp ligand or a rp substrate), and a test compound, e.g., under conditions wherein, but for the test compound, the rp protein and target molecule are able to interact; and (ii) detecting the formation of a complex which includes the rp protein and the target polypeptide either by directly quantitating the complex, by measuring inductive effects of the rp protein, or, in the instance of a substrate, measuring the conversion to product. A statistically significant change, such as a decrease, in the interaction of the rp and target molecule in the presence of a test compound (relative to what is detected in the absence of the test compound) is indicative of a modulation (e.g., inhibition or potentiation of the interaction between the rp protein and the target molecule).

Yet another aspect of the present invention concerns a method for modulating the transcription of certain genes in a cell by modulating rp bioactivity, (e.g., by potentiating or disrupting rp bioactivity). In general, whether carried out in vivo, in vitro, or in situ, the method comprises treating the cell with an effective amount of a rp therapeutic so as to alter, relative to the cell in the absence of treatment, the level of transcription of certain genes Accordingly, the method can be carried out with rp therapeutics such as peptide and peptidomimetics or other molecules identified in the above-referenced drug screens which agonize or antagonize the effects of signaling from a rp protein or ligand binding of a rp protein. Other rp therapeutics include antisense constructs for inhibiting expression of rp proteins, and dominant negative mutants of rp proteins which competitively inhibit ligand interactions upstream and signal transduction downstream of the wild-type rp protein.

A further aspect of the present invention provides a method of determining if a subject is at risk for Rieger Syndrome or other disorder resulting from a mutant rp gene. The method includes detecting, in a tissue of the subject, the presence or absence of a genetic lesion characterized by at least one of (i) a mutation of a gene encoding a rp protein, e.g.a gene represented in one of SEQ ID Nos: 1 or 3 or a homolog thereof; or (ii) the misexpression of a rp gene. In preferred embodiments, detecting the genetic lesion includes ascertaining the existence of at least one of: a deletion of one or more nucleotides from a rp gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of soluble rp protein.

For example, detecting the genetic lesion can include (i) providing a probe/primer comprised of an oligonucleotide which hybridizes to a sense or antisense sequence of a rp gene or naturally occurring mutants thereof, or 5' or 3' flanking sequences naturally associated with the rp gene; (ii) contacting the probe/primer to an appropriate nucleic acid containing sample; and (iii) detecting, by hybridization of the probe/primer to the nucleic acid, the presence or absence of the genetic lesion; e.g. wherein detecting the lesion comprises utilizing the probe/primer to determine the nucleotide sequence of the rp gene and, optionally, of the flanking nucleic acid sequences. For instance, the primer can be employed in a polymerase chain reaction (PCR) or in a ligation chain reaction (LCR). In alternate embodiments, the level of a rp protein is detected in an immunoassay using an antibody which is specifically immunoreactive with the rp protein.

Other features and advantages of the invention will be apparent from the following detailed description and claims.

3. BRIEF DESCRIPTION OF THE FIGURES

FIGS. 1A-1B shows the nucleotide and deduced amino acid sequence of the human rp gene including 5' and 3' untranslated regions. The top line represents the amino acid sequence. The bottom line represents the nucleotide sequence. "*" represents the stop codon.

FIG. 2 shows the nucleotide and deduced amino acid sequence of a human rp gene fragment including a 3' untranslated region. The top line represents the amino acid sequence. The bottom line represents the nucleotide sequence.

FIGS. 3A-3B shows the nucleotide and deduced amino acid sequence of the mouse tub gene including 5' and 3' untranslated regions. The top line represents the amino acid sequence. The bottom line represents the nucleotide sequence.

FIGS. 4A-4B. shows the nucleotide and deduced amino acid sequence of the human tub gene including 5' and 3' untranslated regions. The top line represents the amino acid sequence. The bottom line represents the nucleotide sequence.

4. DETAILED DESCRIPTION OF THE INVENTION

4.1. General

The present invention is based on the discovery of a family of novel genes, referred to herein as "rp." (Retinitis Pigmentosa) genes.

The rp genes or gene products provided by the present invention are exemplified by hrp. The mRNA transcripts including 5' and 3' untranslated regions as well as the coding region; and the deduced amino acid sequences of hrp is shown in FIGS. 1A-1B and in SEQ ID Nos: 1, 2 and 3. The mRNA transcripts including 5' and 3' untranslated regions as well as the coding region; and the deduced amino acid sequences of a human rp gene fragment including a 3' untranslated region is shown in FIG. 2 and in SEQ ID Nos: 4, 5 and 6.

The molecular weight of rp proteins is approximately 38880 daltons. Based on Northern Analysis, the rp gene has been found to mainly be expressed in retinal tissue.

The hrp gene is 56.4% identical to the human tub gene and the hrp protein is 46% identical to htub. Although the N-terminus of the two gene products are dissimilar, the most conserved region of the two gene products are 66.4% identical. Mutations in the tub gene have been determined to cause maturity-onset obesity, insulin resistance and sensory (e.g. eye and ear) and fertility deficits. Based on sequence similarity, the tub and rp genes may perform similar molecular functions in different biochemical pathways or may even function in the same biochemical pathway(s).

Accordingly, certain aspects of the present invention relate to nucleic acid molecules encoding vertebrate rp proteins, rp proteins, antibodies immunoreactive with rp proteins, and preparations of such compositions. In addition, drug discovery assays are provided for identifying agents which can modulate the biological function of rp proteins, such as by altering the interaction of vertebrate rp molecules with either downstream or upstream elements in the signal transduction pathway. Such agents can be useful therapeutically as further described herein. Moreover, the present invention provides diagnostic and therapeutic assays and reagents for detecting and treating disorders involving, for example, aberrant expression (or loss thereof of vertebrate rp genes. Other aspects of the invention are described below or will be apparent to those skilled in the art in light of the present disclosure.

4.2 Definitions

For convenience, the meaning of certain terms and phrases employed in the specification, examples, and appended claims are provided below.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject rp polypeptides with a second amino acid sequence defining a domain (e.g. polypeptide portion) foreign to and not substantially homologous with any domain of one of the rp proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-rp-Y, wherein rp represents a portion of the protein which is derived from one of the rp proteins, and X and Y are independently absent or represent amino acid sequences which are not related to one of the rp sequences in an organism, including naturally occurring mutants.

"Complementary" sequences as used herein refer to sequences which have sufficient complementarity to be able to hybridize, forming a stable duplex.

A "delivery complex" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a rp polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

As used herein, the term "gene" or "recombinant gene" refers to a nucleic acid molecule comprising an open reading frame encoding one of the rp polypeptides of the present invention, including both exon and (optionally) intron sequences. A "recombinant gene" refers to nucleic acid encoding a rp polypeptide and comprising rp-encoding exon sequences, though it may optionally include intron sequences which are either derived from a chromosomal rp gene or from an unrelated chromosomal gene. Exemplary recombinant genes encoding the subject rp polypeptides are represented in the appended Sequence Listing. The term "intron" refers to a DNA sequence present in a given rp gene which is not translated into protein and is generally found between exons.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the rp sequences of the present invention.

The term "interact" as used herein is meant to include detectable interactions between molecules, such as can be detected using, for example, a yeast two hybrid assay. The term interact is also meant to include "binding" interactions between molecules. Interactions may, for example, be protein-protein or protein-nucleic acid in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject rp polypeptides preferably includes no more than 10 kilobases (kb) of nucleic acid sequence which naturally immediately flanks the rp gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation, i.e., stimulation, and downregulation, i.e. suppression, of a response.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant is expressed in some but not all cells of the animal. The term "tissue-specific chimeric animal" indicates that one of the recombinant rp genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding a rp polypeptide is inserted into a suitable expression vector which is in turn used to transform a host cell to produce the heterologous protein. Moreover, the phrase "derived from", with respect to a recombinant rp gene, is meant to include within the meaning of "recombinant protein" those proteins having an amino acid sequence of a native rp protein, or an amino acid sequence similar thereto which is generated by mutations including substitutions and deletions (including truncation) of a naturally occurring form of the protein.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a vertebrate, preferably rp gene, such as a rp sequence designated in one of SEQ ID Nos: 1 or 3, or a sequence complementary thereto, or naturally occurring mutants thereof, such that it shows at least 10 times more hybridization, preferably at least 50 times more hybridization, and even more preferably at least 100 times more hybridization than it does to a cellular nucleic acid (e.g., mRNA or genomic DNA) encoding a protein other than a vertebrate rp protein as defined herein.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant mammalian rp genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of rp proteins.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a mammalian rp polypeptide or, in the case of anti-sense expression from the transferred gene, the expression of a naturally-occurring form of the rp protein is disrupted.

As used herein, the term "transgene" means a nucleic acid sequence (encoding, e.g., one of the mammalian rp polypeptides, or pending an antisense transcript thereto), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the mammalian rp proteins, e.g. either agonistic or antagonistic forms. However, transgenic animals in which the recombinant rp gene is silent are also contemplated, as for example, the FLP or CRE recombinase dependent constructs described below. Moreover, "transgenic animal" also includes those recombinant animals in which gene disruption of one or more rp genes is caused by human intervention, including both recombination and antisense techniques.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred. to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

4.3 Nucleic Acids of the Present Invention

As described below, one aspect of the invention pertains to isolated nucleic acids comprising nucleotide sequences encoding rp polypeptides, and/or equivalents of such nucleic acids. The term equivalent is understood to include nucleotide sequences encoding functionally equivalent rp polypeptides or functionally equivalent peptides having an activity of a vertebrate rp protein such as described herein. Equivalent nucleotide sequences will include sequences that differ by one or more nucleotide substitutions, additions or deletions, such as allelic variants; and will, therefore, include sequences that differ from the nucleotide sequence of the rp gene shown in SEQ ID Nos: 1 or 3 due to the degeneracy of the genetic code.

Preferred nucleic acids are vertebrate rp nucleic acids. Particularly preferred vertebrate rp nucleic acids are mammalian. Regardless of species, particularly preferred rp nucleic acids encode polypeptides that are at least 90% similar to an amino acid sequence of a vertebrate rp. Preferred nucleic acids encode a rp polypeptide comprising an amino acid sequence at least 90% homologous and more preferably 94% homologous with an amino acid sequence of a vertebrate rp, e.g., such as a sequence shown in one of SEQ ID Nos: 1 or 3. Nucleic acids which encode polypeptides at least about 95%, and even more preferably at least about 98–99% similarity with an amino acid sequence represented in one of SEQ ID Nos: 2 or 4 are also within the scope of the invention. In a particularly preferred embodiment, the nucleic acid of the present invention encodes an amino acid rp sequence shown in one of SEQ ID No: 2. In one embodiment, the nucleic acid is a cDNA encoding a peptide having at least one bioactivity of the subject rp polypeptide. Preferably, the nucleic acid includes all or a portion of the nucleotide sequence corresponding to the coding region of SEQ ID Nos: 1 or 3.

Still other preferred nucleic acids of the present invention encode a rp polypeptide which includes a polypeptide sequence corresponding to all or a portion of amino acid residues of SEQ ID No: 3 or of SEQ ID No. 6, e.g., at least 2, 5, 10, 25, 50, 100, 150 or 200 amino acid residues of that region. For example, preferred nucleic acid molecules for use as probes/primer or antisense molecules (i.e. noncoding nucleic acid molecules) can comprise at least about 6, 12, 20, 30, 50, 100, 125, 150 or 200 base pairs in length, whereas coding nucleic acid molecules can comprise about 200, 250, 300, 350, 400, 410, 420, 430, 435 or 440 base pairs.

Another aspect of the invention provides a nucleic acid which hybridizes to a nucleic acid represented by one of SEQ ID Nos: 1 or 3. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a rp nucleic acid of the present invention will bind to one of SEQ ID Nos 1 or 3 under moderately stringent conditions, for example at about 2.0×SSC and about 40° C. In a particularly preferred embodiment, a rp nucleic acid of the present invention will bind to one of SEQ ID Nos: 1, 3 or 4 under high stringency conditions, but will not bind to the nucleic acids shown in SEQ ID Nos: 6, 8, 9 or 11.

Preferred nucleic acids have a sequence at least 75% homologous and more preferably 80% and even more preferably at least 85% homologous with an amino acid sequence of a mammalian rp, e.g., such as a sequence shown in one of SEQ ID Nos: 1 and 3. Nucleic acids at least 90%, more preferably 95%, and most preferably at least about 98–99% homologous with a nucleic sequence represented in one of SEQ ID Nos: 1 and 3 are-of course also within the scope of the invention. In preferred embodiments, the nucleic acid is a mammalian rp gene and in particularly preferred embodiments, includes all or a portion of the nucleotide sequence corresponding to the coding region of one of SEQ ID Nos: 1 or 3.

Nucleic acids having a sequence that differs from the nucleotide sequences shown in one of SEQ ID Nos: 1 or 3 due to degeneracy in the genetic code are also within the scope of the invention. Such nucleic acids encode functionally equivalent peptides (i.e., a peptide having a biological activity of a mammalian rp polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a mammalian rp polypeptide. However, it is expected that DNA sequence polymorphisms that do lead to changes in the amino acid sequences of the subject rp polypeptides will exist among mammalians. One skilled in the art will appreciate that these variations in one or more nucleotides (e.g., up to about 3–5% of the nucleotides) of the nucleic acids encoding polypeptides having an activity of a mammalian rp polypeptide may exist among individuals of a given species due to natural allelic variation.

As indicated by the examples set out below, rp protein-encoding nucleic acids can be obtained from mRNA present in any of a number of eukaryotic cells. It should also be possible to obtain nucleic acids encoding mammalian rp polypeptides of the present invention from genomic DNA from both adults and embryos. For example, a gene encoding a rp protein can be cloned from either a cDNA or a genomic library in accordance with protocols described herein, as well as those generally known to persons skilled in the art. Examples of tissues and/or libraries suitable for isolation of the subject nucleic acids include breast, spleen, thymus, prostate, testes, ovary, small intestine, colon, and peripheral blood cells, among others. A cDNA encoding a rp protein can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a mammalian rp protein can also be cloned using established polymerase chain reaction techniques. in accordance with the nucleotide sequence information provided by the invention. The nucleic acid of the invention can be DNA or RNA. A preferred nucleic acid is a cDNA represented by a sequence selected from the group consisting of SEQ ID Nos: 1 and 3.

4.3.1. Vectors.

This invention also provides expression vectors containing a nucleic acid encoding a rp polypeptide, operably linked to at least one transcriptional regulatory sequence. "Operably linked" is intended to mean that the nucleotide sequence is linked to a regulatory sequence in a manner which allows expression of the nucleotide sequence. Regulatory sequences are art-recognized and are selected to direct expression of the subject mammalian rp proteins. Accordingly, the term "transcriptional regulatory sequence" includes promoters, enhancers and other expression control elements. Such regulatory sequences are described in Goeddel; *Gene Expression Technology: Methods in Enzymology* 185, Academic Press, San Diego, Calif. (1990). In one embodiment, the expression vector includes a recombinant gene encoding a peptide having an agonistic activity of a subject rp polypeptide, or alternatively, encoding a peptide which is an antagonistic form of the rp protein. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject mammalian rp proteins. Thus, another aspect of the invention features expression vectors for in vivo or in vitro transfection and expression of a mammalian rp polypeptide in particular cell types so as to reconstitute the function of, or alternatively, abrogate the function of rp-induced signaling in a tissue. This could be desirable, for example, when the naturally-occurring form of the protein is misexpressed; or to deliver a form of the protein which alters differentiation of tissue. Expression vectors may also be employed to inhibit neoplastic transformation.

In addition to viral transfer methods, such as those illustrated above, non-viral methods can also be employed to cause expression of a subject rp polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject rp polypeptide gene by the targeted cell. Exemplary targeting means of this type include liposomal derived systems, poly-lysine conjugates, and artificial viral envelopes.

4.3.2. Probes and Primers

Moreover, the nucleotide sequences determined from the cloning of rp genes from mammalian organisms will further allow for the generation of probes and primers designed for use in identifying and/or cloning rp homologs in other cell types, e.g. from other tissues, as well as rp homologs from other mammalian organisms. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence selected from the group consisting of SEQ ID No:1 and 3, or naturally occurring mutants thereof. For instance, primers based on the nucleic acid represented in SEQ ID Nos:1 and 3 can be used in PCR reactions to clone rp homologs. Preferred primers of the invention are set forth as SEQ ID NOs. 12 and 13.

Likewise, probes based on the subject rp sequences can be used to detect transcripts or genomic sequences encoding the same or homologous proteins In preferred embodiments, the probe further comprises a label group attached thereto and able to be detected, e.g. the label group is selected from amongst radioisotopes, fluorescent compounds, enzymes, and enzyme co-factors.

As discussed in more detail below, such probes can also be used as a part of a diagnostic test kit for identifying cells or tissue which misexpress a rp protein, such as by measuring a level of a rp-encoding nucleic acid in a sample of cells from a patient, e.g. detecting rp mRNA levels or determining whether a genomic rp gene has been mutated or deleted. Briefly, nucleotide probes can be generated from the subject rp genes which facilitate histological screening of intact tissue and tissue samples for the presence (or absence) of rp-encoding transcripts. Similar to the diagnostic uses of anti-rp antibodies, the use of probes directed to rp messages, or to genoiuc rp sequences, can be used for both predictive and therapeutic evaluation of allelic mutations which might be manifest in, for example, neoplastic or hyperplastic disorders (e.g. unwanted cell growth) or abnormal differentiation of tissue. Used in conjunction with immunoassays as described herein, the oligonucleotide probes can help facilitate the determination of the molecular basis for a developmental disorder which may involve some abnormality associated with expression (or lack thereof) of a rp protein. For instance, variation in polypeptide synthesis can be differentiated from a mutation in a coding sequence.

4.3.3. Antisense, Ribozyme and Triplex Techniques

One aspect of the invention relates to the use of the isolated nucleic acid in "antisense" therapy. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject rp proteins so as to inhibit expression of that protein, e.g. by inhibiting transcription and/or translation. The binding may be by conventional base pair complementarity, or, for example, in the case of binding to DNA duplexes, through specific interactions in the maior groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a mammalian rp protein. Alternatively, the antisense construct is an oligonucleotide probe which is generated ex vivo and which, when introduced into the cell causes inhibition of expression by hybridizing with the mRNA and/or genomic sequences of a mammalian rp gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668. With respect to antisense DNA, oligodeoxyribonucleotides derived from the translation initiation site, e.g., between the −10 and +10 regions of the rp nucleotide sequence of interest, are preferred.

Antisense approaches involve the design of oligonucleotides (either DNA or RNA) that are complementary to rp mRNA. The antisense oligonucleotides will bind to the rp mRNA transcripts and prevent translation. Absolute complementarity, although preferred, is not required. a sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. *Nature* 372:333). Therefore, oligonucleotides complementary to either the 5' or 3' untranslated, non-coding regions of a rp gene could be used in an antisense approach to inhibit translation of endogenous rp mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5',3' or coding region of rp mRNA, antisense nucleic acids should be at least six nucleotides in length, and are preferably oligonucleotides ranging from 6 to about 50 nucleotides in length. In certain embodiments, the-oligonucleotide is at least 10 nucleotides, at least 17 nucleotides, at least 25 nucleotides, or at least 50 nucleotides.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, *Proc. Natl. Acad. Sci.* 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, *BioTechniques* 6:958–976) or intercalating agents. (See, e.g., Zon, 1988, *Pharm. Res.* 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety hich is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An ac-anomeric oligonucleotide forms specific double-stranded hybrids with complementary RNA in which, contrary to the usual β-units, the strands run parallel to each other (Gautier et al., 1987, *Nucl. Acids Res.* 15:6625–6641). The oligonucleotide is a 2'-0-methylribonucleotide (Inoue et al., 1987, *Nucl. Acids Res.* 15:6131–6148), or a chimeric RNA-DNA analogue (Inoue et al., 1987, *FEBS Lett.* 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, *Nucl. Acids Res.* 16:3209), methylphosphonate olgonucleotides can be prepared by use of controlled pore glass polymer supports (Sarin et al., 1988, *Proc. Natl. Acad. Sci. U.S.A.* 85:7448–7451), etc.

While antisense nucleotides complementary to the rp coding region sequence could be used, those complementary to the transcribed untranslated region are most preferred. For example, an antisense oligonucleotide as set forth in SEQ ID No. 14 can be utilized in accordance with the invention.

The antisense molecules should be delivered to cells which express the rp in vivo. A number of methods have been developed for delivering antisense DNA or RNA to cells; e.g., antisense molecules can be injected directly into the tissue site, or modified antisense molecules, designed to target the desired cells (es, antisense linked to peptides or antibodies that specifically bind receptors or antigens expressed on the target cell surface) can be administered systematically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous rp transcripts and thereby prevent translation of the rp mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, *Nature* 290:304–310), the promoter contained in the 3' long terminal repeat of Rous sarcoma virus (Yamamoto et al., 1980, *Cell* 22:787–797), the herpes thymidine kinase promoter (Wagner et al., 1981, *Proc. Natl. Acad Sci. U.S.A.* 78:1441–1445), the regulatory sequences of the metallothionein gene (Brinster et al, 1982, *Nature* 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpesvirus vectors may be used), in which case administration may be accomplished by another route (e.g., systematically).

Ribozyme molecules designed to catalytically cleave rp mRNA transcripts can also be used to prevent translation of rp mRNA and expression of rp. (See, e.g., PCT International Publication WO90/11364, published Oct. 4, 1990; Sarver et al., 1990, Science 247:1222–1225). While ribozymes that cleave mRNA at site specific recognition sequences can be used to destroy rp mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, *Nature*, 334:585–591. There are hundreds of potential hammerhead ribozyme cleavage sites within the nucleotide sequence of human rp cDNA (FIG. 3). Preferably the ribozyme is engineered so that the cleavage recognition site is located near the 5' end of the rp mRNA; i.e., to increase efficiency and minimize the intracellular accumulation of non-functional mRNA transcripts.

For example, ribozymes having the sequence set forth in SEQ ID NO 13 can be utilized in accordance with the invention. The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, *Science*, 224:574–578; Zaug and Cech, 1986, *Science*, 231:470–475; Zaug, et al., 1986, Nature, 324:429–433; published International patent application No. WO88/04300 by University Patents Inc.; Been and Cech, 1986, *Cell*, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in rp.

As in the antisense approach, the ribozymes can be composed of modified oligonucleotides (e.g. for improved stability, targeting, etc.) and should be delivered to cells which express the rp in vivo e.g., hypothalamus and/or the choroid plexus. A preferred method of delivery involves using a DNA construct "encoding" the robozyme under the control of a strong constitutive pol III or pol II promoter, so that transfected cells will produce sufficient quantities of the ribozyme to destroy endogenous rp messages and inhibit translation. Because ribozymes unlike antisense molecules, are catalytic, a lower intracellular concentration is required for efficiency.

Endogenous rp gene expression can also be reduced by inactivating or "knocking out" the rp gene or its promoter using targeted homologous recombination. (E.g., see Smithies et al., 1985, *Nature* 317:230–234; Thomas & Capecchi, 1987, *Cell* 51:503–512; Thompson et al., 1989 *Cell* 5:313–321; each of which is incorporated by reference herein in its entirety). For example, a mutant, non-functional rp (or a completely unrelated DNA sequence) flanked by DNA homologous to the endogenous rp gene (either the coding regions or regulatory regions of the rp gene) can be used, with or without a selectable marker and/or a negative selectable marker, to transfect cells that express rp in vivo. Insertion of the DNA construct, via targeted homologous recombination, results in inactivation of the rp gene. Such approaches are particularly suited in the agricultural field where modifications to ES (embryonic stem) cells can be used to generate animal offspring with an inactive rp (e.g., see Thomas & Capecchi 1987 and Thompson 1989, supra). However this approach can be adapted for use in humans provided the recombinant DNA constructs are directly administered or targeted to the required site in vivo using appropriate viral vectors, es., herpes virus vectors for delivery to brain tissue; e.g., the hypothalamus and/or choroid plexus.

Alternatively, endogenous rp gene expression can be reduced by targeting deoxyribonucleotide sequences complementary to the regulatory region of the rp gene (i.e., the rp promoter and/or enhancers) to form triple helical structures that prevent transcription of the rp gene in target cells in the body. (See generally, Helene, C. 1991, *Anticancer Drug Des.*, 6(6):569–84; Helene, C., et al., 1992, Ann, N.Y. *Accad. Sci.*, 660:27–36; and Maher, L. J., 1992, *Bioassays* 14(12):807–15).

Likewise, the antisense constructs of the present invention, by antagonizing the normal biological activity of one of the rp proteins, can be used in the manipulation of tissue, e.g. tissue differentiation, both in vivo and for ex vivo tissue cultures.

Furthermore, the anti-sense techniques (e.g. microinjection of antisense molecules, or transfection with plasmids whose transcripts are anti-sense with regard to a rp mRNA or gene sequence) can be used to investigate role of rp in developmental events, as well as the normal cellular function of rp in adult tissue. Such techniques can be utilized in cell culture, but can also be used in the creation of transgenic animals, as detailed below.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding FCHD534 interactor proteins.

Specific ribozyme cleavage sites within any potential RNA target are initially identified by scanning the molecule of interest for ribozyme cleavage sites which include the following sequences, GUA, GWU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

4.4. Polypeptides of the Present Invention

The present invention also makes available isolated rp polypeptides which are isolated from, or otherwise substantially free of other cellular proteins, especially other signal transduction factors and/or transcription factors which may normally be associated with the rp polypeptide. The term "substantially free of other cellular proteins" (also referred to herein as "contaminating proteins") or "substantially pure or purified preparations" are defined as encompassing preparations of rp polypeptides having less than about 20% (by dry weight) contaminating protein, and preferably having less than about 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified rp preparations will lack any contaminating proteins from the same animal from which rp is normally produced, as can be accomplished by recombinant expression of, for example, a human rp protein in a non-human cell.

Full length proteins or fragments corresponding to one or more particular motifs and/or domains or to arbitrary sizes, for example, at least 5, 10, 25, 50, 75, 100, 125, 150 amino acids in length are within the scope of the present invention.

For example, isolated rp polypeptides can include all or a portion of an amino acid sequences corresponding to a rp polypeptide represented in one or more of SEQ ID No:2 and 4. Isolated peptidyl portions of rp proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a rp polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") rp protein.

Another aspect of the present invention concerns recombinant forms of the rp proteins. Recombinant polypeptides preferred by the present invention, in addition to native rp proteins, are at least 92% homologous and more preferably 94% homologous and most preferably 95% homologous with an amino acid sequence represented by any of SEQ ID Nos: 2 or 4. Polypeptides which are at least about 98–99% homologous with a sequence selected from the group consisting of SEQ ID Nos: 2 or 4 are also within the scope of the invention. In a preferred embodiment, a rp protein of the present invention is a mammalian rp protein. In a particularly preferred embodiment a rp protein comprises the coding sequence of one of SEQ ID Nos.: 2 or 4. In particularly preferred embodiments, a rp protein. has a rp bioactivity.

In certain preferred embodiments, the invention features a purified or recombinant rp polypeptide having a molecular weight of approximately 17 kD. It will be understood that certain post-translational modifications, e.g., phosphorylation and the like, can increase the apparent molecular weight of the rp protein relative to the unmodified polypeptide chain.

The present invention further pertains to recombinant forms of one of the subject rp polypeptides which are encoded by genes derived from a mammalian organism, and which have amino acid sequences evolutionarily related to the rp proteins represented in SEQ ID Nos: 2 and 4. Such recombinant rp polypeptides preferably are capable of functioning in one of either role of an agonist or antagonist of at least one biological activity of a wild-type ("authentic") rp protein of the appended sequence listing. The term "evolutionarily related to", with respect to amino acid sequences of mammalian rp proteins, refers to both polypeptides having amino acid sequences which have arisen naturally, and also to mutational variants of mammalian rp polypeptides which are derived, for example, by combinatorial mutagenesis. Such evolutionarily derived rp polypeptides preferred by the resent invention have a rp bioactivity and are at least 92% homologous and more preferably 94% homologous and most preferably 98–99% homologous with the amino acid sequence selected from the group consisting. of SEQ ID Nos: 2 and 4. In a particularly preferred embodiment, a rp protein comprises the amino acid coding sequence of one of SEQ ID No: 2 or 4.

In general, polypeptides referred to herein as having an activity (e.g., are "bioactive") of a mammalian rp protein are defined as polypeptides which include an amino acid sequence corresponding (e.g., identical or homologous) to all or a portion of the amino acid sequences of a mammalian rp proteins shown in any one or more of SEQ ID Nos: 2 or 4 and which mimic or antagonize all or a portion of the biologicalibiochemical activities of a naturally occurring rp protein. In preferred embodiments, the biochemical activities are related to gene expression, pituitary development, and abdominal development related to umbilical and vitelline artery expression.

Other biological activities of the subject rp proteins are described herein or will be reasonably apparent to those skilled in the art. According to the present invention, a polypeptide has biological activity if it is a specific agonist or antagonist of a naturally-occurring form of a mammalian rp protein.

The present invention further pertains to methods of producing the subject rp polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant rp polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant rp polypeptide is a fusion protein containing a domain which facilitates its purification, such as GST fusion protein or poly(His) fusion protein.

Moreover, it will be generally appreciated that, under certain circumstances, it may be advantageous to provide homologs of one of the subject rp polypeptides which function in a limited capacity as one of either a rp agonist (mimetic) or a rp antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of rp proteins.

Homologs of each of the subject rp proteins can be generated by mutagenesis, such as by discrete point mutation(s), or by truncation. For instance, mutation can give rise to homologs which retain substantially the same, or merely a subset, of the biological activity of the rp polypeptide from which it was derived. Alternatively, antagonistic forms of the protein can be generated which are able to inhibit the function of the naturally occurring form of the protein, such as by competitively binding to a downstream or upstream member of the biochemical pathway, which includes the rp protein. In addition, agonistic forms of the protein may be generated which are constituatively active. Thus, the mammalian rp protein and homologs thereof provided by the subject invention may be either positive or negative regulators of gene expression.

The recombinant rp polypeptides of the present invention also include homologs of the authentic rp proteins, such as versions of those protein which are resistant to proteolytic cleavage, as for example, due to mutations which alter ubiquitination or other enzymatic targeting associated with the protein.

Rp polypeptides may also be chemically modified to create rp derivatives by forming covalent or aggregate conjugates with other chemical moieties, such as glycosyl groups, lipids, phosphate, acetyl groups and the like. Covalent derivatives of rp proteins can be prepared by linking the chemical moieties to functional groups on amino acid sidechains of the protein or at the N-terminus or at the C-terminus of the polypeptide.

Modification of the structure of the subject mammalian rp polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the rp polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, WH Freeman and Co.: 1981). Whether a change in the amino acid sequence of a peptide results in a functional rp homolog (e.g. functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject rp proteins as well as truncation mutants, and is especially useful for identifying potential variant sequences (e.g. homologs) that are functional in modulating gene expression. The purpose of screening such combinatorial libraries is to generate, for example, novel rp homologs which can act as either agonists or antagonist, or alternatively, possess novel activities all together.

Likewise, rp homologs can be generated by the present combinatorial approach to selectively inhibit gene expression. For instance, mutagenesis can provide rp homologs which are able to bind other signal pathway proteins (or DNA) yet prevent propagation of the signal, e.g. the homologs can be dominant negative mutants. Moreover, manipulation of certain domains of rp by the present method can provide domains more suitable for use in fusion proteins.

In one embodiment, the variegated library of rp variants is generated by combinatorial mutagenesis at the nucleic acid. level, and is encoded by a variegated gene library. For instance, a mixture of synthetic oligonucleotides can be enzymatically ligated into gene sequences such that the degenerate set of potential rp sequences are expressible as individual polypeptides, or alternatively, as a set of larger fusion proteins (e.g. for phage display) containing the set of rp sequences therein.

There are many ways by which such libraries of potential rp homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential rp sequences. The synthesis of degenerate oligonucleotides is well known in the art (see for example, Narang, SA (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Likewise, a library of coding sequence fragments can be provided for a rp clone in order to generate a variegated population of rp fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a rp coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of rp homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate rp sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature*, 2., In Maenner and Manderick, eds., Elsevier Publishing Co., Amsterdam, pp. 401–410; Delgrave et al., 1993, *Protein Engineering* 6(3):327–331).

The invention also provides for reduction of the vertebrate rp proteins to generate mimetics, e.g. peptide or non-peptide agents, which are able to disrupt binding of a mammnalian rp polypeptide of the present invention with either upstream or downstream components. Thus, such mutagenic techniques as described above are also useful to map the determinants of the rp proteins which participate in protein-protein interactions involved in, for example, binding of the subject rp polypeptide to proteins which may function upstream (including both activators and repressors of its activity) or to proteins or nucleic acids which may function downstream of the rp polypeptide, whether they are positively or negatively regulated by it. To illustrate, the critical residues of a subject rp polypeptide which are involved in molecular recognition of a component upstream or downstream of a rp can be determined and used to generate rp-derived peptidomimetics which competitively inhibit binding of the authentic rp protein with that moiety. By employing, for example, scanning mutagenesis to map the amino acid residues of each of the subject rp proteins which are involved in binding other extracellular proteins, peptidomimetic compounds can be generated which mimic those residues of the rp protein which facilitate the interaction. Such mimetics may then be used to interfere with the normal function of a rp protein. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamnma lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-tum dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

4.4.1. Cells Expressing Recombinant rp Polyieptides.

This invention also pertains to a host cell transfected to express a recombinant form of the subject rp polypeptides. The host cell may be any prokaryotic or eukaryotic cell. Thus, a nucleotide sequence derived from the cloning of mammalian rp proteins, encoding all or a selected portion of the full-length protein, can be used to produce a recombinant form of a rp polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. MAP kinase, p53, WT1, PTP phosphotases, SRC, and the like. Similar procedures, or modifications thereof, can be employed to prepare recombinant rp polypeptides by microbial means or tissue-culture technology in accord with the subject invention.

The recombinant rp genes can be produced by ligating nucleic acid encoding a rp protein, or a portion thereof, into a vector suitable for expression in either prokaryotic cells, eukaryotic cells, or both. Expression vectors for production of recombinant forms of the subject rp polypeptides include plasmids and other vectors. For instance, suitable vectors for the expression of a rp polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a rp polypeptide is produced recombinantly utilizing an expression vector generated by sub-cloning the coding sequence of one of the rp genes represented in SEQ ID Nos: 1 and 3.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16and 17.

In some instances, it may be desirable to express the recombinant rp polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a rp protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing rp-derived polypeptides in a host which produces MAP (e.g., *E. coli* or CM89 or *S. cerevisiae*), or in vitro by use of purified MAP (e.g., procedure of Miller et al., supra).

In other embodiments transgenic animals, described in more detail below could be used to produce recombinant proteins.

4.4.2 Fusion Proteins and Immunoiens.

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a rp protein. For example, the VP6 capsid protein of rotavirus can be used as an immunologic carrier protein for portions of the rp polypeptide, either in the monomeric form or in the form of a viral particle. The nucleic acid sequences corresponding to the portion of a subject rp protein to which antibodies are to be raised can be incorporated into a fusion gene construct which includes coding sequences for a late vaccinia virus structural protein to produce a set of recombinant viruses expressing fusion proteins comprising rp epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a rp protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized to generate an immunogen, wherein a desired portion of a rp polypeptide is obtained directly from organo-chemical synthesis of the peptide onto an oligomeric branching lysine core (see, for example, Posnett et al. (1988) JBC 263:1719 and Nardelli et al. (1992) *J. Immunol.* 148:914). Antigenic determinants of rp proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the mammalian rp polypeptides of the present invention. For example, rp polypeptides can be generated as glutathione-S-transferase (GST-fusion) proteins. Such GST-fusion proteins can enable easy purification of the rp polypeptide, as for example by the use of glutathione-derivatized matrices (see, for example, *Current Protocols in Molecular Biology*, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

4.4.3. Antibodies

Another aspect of the invention pertains to an antibody specifically reactive with a rp protein. For example, by using immunogens derived from a rp protein, e.g. based on the cDNA sequences, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., a rp polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of a rp protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a rp protein of a mammal, e.g. antigenic determinants of a protein represented by SEQ ID Nos:2 or 4 or closely related homologs (e.g. at least 92% homologous, and more preferably at least 94% homologous).

Following immunization of an animal with an antigenic preparation of a rp polypeptide, anti- rp antisera can be obtained and, if desired, polyclonal anti- rp antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature,* 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with a rp polypeptide of the present invention and monoclonal antibodies isolated from a culture comprising such hybridoma cells. In one embodiment anti-human antibodies specifically react with the proteins encoded by the DNA of ATCC deposit 98144 or 98147.

The term antibody as used herein is intended to include fragments thereof which are also specifically reactive with one of the subject mammalian rp polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific and chimeric molecules having affinity for a rp protein conferred by at least one CDR region of the antibody.

Antibodies which specifically bind rp epitopes can also be used in immunohistochemical staining of tissue samples in order to evaluate the abundance and pattern of expression of each of the subject rp polypeptides. Anti-rp antibodies can be used diagnostically in immuno-precipitation and immuno-blotting to detect and evaluate rp protein levels in tissue as part of a clinical testing procedure. For instance, such measurements can be useful in predictive valuations of the onset or progression of proliferative disorders. Likewise, the ability to monitor rp protein levels in an individual can allow determination of the efficacy of a given treatment regimen for an individual afflicted with such a disorder. The level of rp polypeptides may be measured from cells in bodily fluid, such as in samples of cerebral spinal fluid or amniotic fluid, or can be measured in tissue, such as produced by biopsy. Diagnostic assays using anti- rp antibodies can include, for example, immunoassays designed to aid in early diagnosis of a degenerative disorder, particularly ones which are manifest at birth. Diagnostic assays using anti- rp polypeptide antibodies can also include immunoassays designed to aid in early diagnosis and phenotyping neoplastic or hyperplastic disorders.

Another application of anti-rp antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a rp protein, e.g. other orthologs of a particular rp protein or other paralogs from the same species, can then be detected with antibodies, as, for example, reacting nitrocellulose filters lifted from infected plates with anti-rp antibodies. Positive phage detected by this assay can then be isolated from the infected plate. Thus, the presence of rp homologs can be detected and cloned from other animals, as can alternate isoforms (including splicing variants) from humans.

4.5 Methods of Treating Disease

There may be a variety of pathological conditions for which rp therapeutics of the present invention can be used in treatment. Examples include: Retinitis Pigmentosa and weight disorders such as obesity, cachexia and anorexia.

A "rp therapeutic," whether an antagonist or agonist of wild type rp, can be, as appropriate, any of the preparations described above, including isolated polypeptides, gene therapy constructs, antisense molecules, peptidomimetics or agents identified in the drug assays provided herein.

Since, in some cases, genes may be upregulated in a disease state and in other cases may be downregulated, it will be desirable to activate and/or potentiate or suppress and/or downmodulate rp bioactivity depending on the condition to be treated using the techniques compounds and methods described herein. Some genes may be underexpressed in certain disease states. Several genes are now known to be down-regulated in monocytes under disease conditions. For example, bc1-2 and glutathione peroxidase gene expression is down-regulated in the monocytes of patients exposed to a high lipid diet, e.g. cholesterol or fat, that leads to high serum LDL levels. The activity of rp gene products may be in some way impaired, leading to the development of disease symptoms. Such down-regulation of rp gene expression or decrease in the activity of a rp protein may have a causative or exacerbating effect on the disease state.

Among the approaches which may be used to ameliorate disease symptoms involving the misexpression of a rp gene are, for example, antisense, ribozyme, and triple helix molecules described above. Compounds that compete with an rp protein for binding to upstream or downstream element in a signaling cascade will antagonize a rp protein, thereby inducing a therapeutic effect. Examples of suitable compounds include the antagonists or homologues described in detail above. In other instances, the increased expression or bioactivity of a rp protein may be desirable and may be accomplished by, for example the use of the rp agonists or mimetics or by gene replacement therapy, as described herein.

Compounds identified as increasing or decreasing rp gene expression or protein activity can be administered to a subject at therapeutically effective dose to treat or ameliorate a disease or condition.

4.5.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.5.2. Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

In clinical settings, the gene delivery systems for the therapeutic rp gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057). A rp gene, such as any one of the sequences represented in the group consisting of SEQ ID NO: 1 or 3, or a sequence homologous thereto can be delivered in a gene therapy construct by electroporation using techniques described, for example, by Dev et al. ((1994) *Cancer Treat Rev* 20:105–115). Gene therapy vectors comprised of viruses that provide specific effective and highly localized treatment of eye diseases are described in Published International Patent Application No. WO 95/34580 to U. Eriksson et al.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.6 Diagnostic and Prognostic Assays

In the diagnostic and prognostic assays described herein, in addition to the rp nucleic acid molecules and polypeptides described above, the present invention provides for the use of nucleic comprising at least a portion of the nucleic acid sequence shown in SEQ ID Nos: 1 or 3 or polypeptides comprising at least a portion of the amino acid sequence shown in SEQ ID No:2.

The present method provides a method for determining if a subject is at risk for Retinitis Pigmentosa or a weight disorder (e.g. obesity, cachexia or anorexia). In preferred embodiments, the methods can be characterized as comprising detecting, in a sample of cells from the subject, the presence or absence of a genetic lesion characterized by at least one of (i) an alteration affecting the integrity of a gene encoding a rp-protein, or (ii) the mis-expression of the rp gene. To illustrate, such genetic lesions can be detected by ascertaining the existence of at least one of (i) a deletion of one or more nucleotides from a rp gene, (ii) an addition of one or more nucleotides to a rp gene, (iii) a substitution of one or more nucleotides of a rp gene, (iv) a gross chromosomal rearrangement of a rp gene, (v) a gross alteration in the level of a messenger RNA transcript of a rp gene, (vii) aberrant modification of a rp gene, such as of the methylation pattern of the genomic DNA, (vii) the presence of a non-wild type splicing pattern of a messenger RNA transcript of a rp gene, (viii) a non-wild type level of a rp-protein, (ix) allelic loss of a rp gene, and (x) inappropriate post-translational modification of a rp-protein. As set out below, the present invention provides a large number of assay techniques for detecting lesions in a rp gene, and importantly, provides the ability to discern between different molecular causes underlying rp-dependent aberrant cell growth, proliferation and/or differentiation.

In an exemplary embodiment, there is provided a nucleic acid composition comprising a (purified) oligonucleotide probe including a region of nucleotide sequence which is capable of hybridizing to a sense or antisense sequence of a rp gene, such as represented by any of SEQ ID Nos: 1 and 3, or naturally occurring mutants thereof, or 5' or 3' flanking sequences or intronic sequences naturally associated with the subject rp genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

As set out above, one aspect of the present invention relates to diagnostic assays for determining, in the context of cells isolated from a patient, if mutations have arisen in one or more rp of the sample cells. The present method provides a method for determining if a subject is at risk for a disorder characterized by aberrant cell proliferation and/or differentiation. In preferred embodiments, the method can be generally characterized as comprising detecting, in a sample of cells from the subject, the presence or absence of a genetic lesion characterized by an alteration affecting the integrity of a gene encoding a rp. To illustrate, such genetic lesions can be detected by ascertaining the existence of at least one of (i) a deletion of one or more nucleotides from a rp-gene, (ii) an addition of one or more nucleotides to a rp-gene, (iii) a substitution of one or more nucleotides of a rp-gene, and (iv) the presence of a non-wild type splicing pattern of a messenger RNA transcript of a rp-gene. As set out below, the present invention provides a large number of assay techniques for detecting lesions in rp genes, and importantly, provides the ability to discern between different molecular causes underlying rp-dependent aberrant cell growth, proliferation and/or differentiation.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the rp-gene (see Abravaya et al. (1995) *Nuc Acid Res* 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a rp gene under conditions such that hybridization and amplification of the rp-gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in a rp gene from a sample cell are identified by alterations -in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the rp gene and detect mutations by comparing the sequence of the sample rp with the corresponding wild-type (control) sequence. Exemplary sequencing reactions include those based on techniques developed by Maxim and Gilbert (*Proc. Natl Acad Sci USA* (1977) 74:560) or Sanger (Sanger et al (1977) *Proc. Nat. Acad. Sci* 74:5463). It is also contemplated that any of a variety of automated sequencing procedures may be utilized when performing the subject assays (*Biotechniques* (1995) 19:448), including by sequencing by mass spectrometry (see, for example PCT publication WO 94/16101; Cohen et al. (1996) *Adv Chromatogr* 36:127–162; and Griffin et al. (1993) *Appl Biochem Biotechnol* 38:147–159). It will be evident to one skilled in the art that, for certain embodiments, the occurence of only one, two or three of the nucleic acid bases need be determined in the sequencing reaction. For instance, A-tract or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA heteroduplexes (Myers, et al. (1985) *Science* 230:1242). In general, the art technique of "mismatch cleavage" starts by providing heteroduplexes of formed by hybridizing (labelled) RNA or DNA containing the wild-type rp sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) Methods Enzymod. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in rp cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a rp sequence, e.g., a wild-type rp sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in rp genes. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125–144; and Hayashi (1992) *Genet Anal Tech Appl* 9:73–79). Single-stranded DNA fragments of sample and control rp nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al (1989) *Proc. Natl Acad. Sci USA* 86:6230). Such allele speicific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) *Nucleic Acids Res.* 17:2437–2448) or at the extreme 3' end of one primer. where, under appropriate conditions, mismatch can prevent, or reduce polymerase extension (Prossner (1993) *Tibtech* 11:238. In addition it may be desirable to introduce a novel restriction site in the region of the mutation to create cleavage-based detection (Gasparini et al (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

For mutations that produce premature termination of protein translation, the protein truncation test (PTT) offers an efficient diagnostic approach (Roest, et. al., (1993) *Hum. Mol. Genet.* 2:1719–21; van der Luijt, et. al., (1994) *Genomics* 20:1–4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Another embodiment of the invention provides for a nucleic acid composition comprising a (purified) oligonucleotide probe including a region of nucleotide sequence which is capable of hybridizing to a sense or antisense sequence of a rp-gene, or naturally occurring mutants thereof, or 5' or 3' flanking sequences or intronic sequences naturally associated with the subject rp-genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels. Such oligonucleotide probes can be used for both predictive and therapeutic evaluation of allelic mutations which might be manifest in, for example, neoplastic or hyperplastic disorders (e.g. aberrant cell growth).

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a rp gene.

Any cell type or tissue, preferably monocytes, endothelial cells, or smooth muscle cells, in which the rp is expressed may be utilized in the diagnostics described below. For example, a subject's bodily fluid (e.g. blood) can be obtained by known techniques (e.g. venipuncture). Alternatively, nucleic acid tests can be performed on dry samples (e.g. hair or skin). Fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant rp proteins, which are discussed, above, may also be used indisease diagnostics and prognostics. Such diagnostic methods, may be used to detect abnormalities in the level of rp protein expression, or abnormalities in the structure and/or tissue, cellular, or subcellular location of rp protein. Structural differences may include, for example, differences in the size, electronegativity, or antigenicity of the mutant rp protein relative to the normal rp protein. Protein from the tissue or cell type to be analyzed may easily be detected or isolated using techniques which are well known to one of skill in the art, including but not limited to western blot analysis. For a detailed explanation of methods for carrying out western blot analysis, see Sambrook et al, 1989, supra, at Chapter 18. The protein detection and isolation methods employed herein may also. be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of rp proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the rp protein, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test. strip, etc. Preferred supports include polystyrene beads. Those skilled in the art will know many other suitable carriers for binding antibody or antigen, or will be able to ascertain the same by use of routine experimentation.

One means for labeling an anti-rp protein specific antibody is via linkage to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a rp gene or gene product can be used to monitor the course of treatment or therapy.

4.7. Drug Screening Assays

In drug screening assays described herein, in addition to the rp nucleic acid molecules and polypeptides described above, the present invention also provides for the use of nucleic comprising at least a portion of the nucleic acid sequence shown in SEQ ID No:1 or polypeptides comprising at least a portion of the amino acid sequence shown in SEQ ID No:2.

Furthermore, by making available purified and recombinant rp polypeptides, the present invention facilitates the development of assays which can be used to screen for drugs, including rp homologs, which are either agonists or antagonists of the normal cellular function of the subject rp polypeptides, or of their role in the pathogenesis of cellular differentiation and/or proliferation and disorders related thereto. In one embodiment, the assay evaluates the ability of a compound to modulate binding between a rp polypeptide and a molecule, be it protein or DNA, that interacts either upstream or downstream of the rp polypeptide in the TGFO signaling pathway. A variety of assay formats will suffice and, in light of the present inventions, will be comprehended by a skilled artisan.

4.7.1 Cell-free Assays

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, the compound of interest is contacted with proteins which may function upstream (including both activators and repressors of its activity) or to proteins or nucleic acids which may function downstream of the rp polypeptide, whether they are positively or negatively regulated by it. To the mixture of the compound and the upstream or downstream element is then added a composition containing a rp polypeptide. Detection and quantification of complexes of rp with it's upstream or downstream elements provide a means for determining a compound's efficacy at inhibiting (or potentiating) complex formation between rp and the rebinding elements. The efficacy of the compound can be assessed by generating dose response curves from data obtained using various concentrations of the test compound. Moreover, a control assay can also be performed to provide a baseline for comparison. In the control assay, isolated and purified rp polypeptide is added to a composition containing the rebinding element, and the formation of a complex is quantitated in the absence of the test compound.

Complex formation between the rp polypeptide and a rp binding element may be detected by a variety of techniques. Modulation of the formation of complexes can be quantitated using, for example, detectably labeled proteins such as radiolabeled, fluorescently labeled, or enzymatically labeled rp polypeptides, by immunoassay, or by chromatographic detection.

Typically, it will be desirable to immobilize either rp or its binding protein to facilitate separation of complexes from uncomplexed forms of one or both of the proteins, as well as to accommodate automation of the assay. Binding of rp to an upstream or downstream element, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/rp (GST/rp) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of rp-binding protein found in the bead fraction quantitated from the gel using standard electrophoretic techniques such as described in the appended examples.

Other techniques for immobilizing proteins on matrices are also available for use in the subject assay. For instance, either rp or its cognate binding protein can be immobilized utilizing conjugation of biotin and streptavidin. For instance, biotinylated rp molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with rp but which do not interfere with binding of upstream or downstream elements can be derivatized to the wells of the plate, and rp trapped in the wells by antibody conjugation. As above, preparations of a rp-binding protein and a test compound are incubated in the rp-presenting wells of the plate, and the amount of complex trapped in the well can be quantitated. Exemplary methods for detecting such complexes, in addition to those described above for the GST-immobilized complexes, include immunodetection of complexes using antibodies reactive with the rp binding element, or which are reactive with rp protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the rp-BP. To illustrate, the rp-BP can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunddetection for quantitating one of the proteins trapped in the complex, antibodies against the protein, such as anti-rp antibodies, can be used. Alternatively, the protein to be detected in the complex can be "epitope tagged" in the form of a fusion protein which includes, in addition to the rp sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, NJ).

4.7.2. Cell Based Assays

In addition to cell-free assays, such as described above, the readily available source of mammalian rp proteins provided by the present invention also facilitates the generation of cell-based assays for identifying small molecule agonists/antagonists and the like. For example, cells which are sensitive to TGFO signals can be caused to overexpress a recombinant rp protein in the presence and absence of a test agent of interest, with the assay scoring for modulation in rp responses by the target cell mediated by the test agent. As with the cell-free assays, agents which produce a statistically significant change in rp-dependent responses (either inhibition or potentiation) can be identified. In an illustrative embodiment, the expression or activity of a rp is modulated embryos or cells and the effects of compounds of interest on the readout of interest (such as tissue differentiation, proliferation, tumorigenesis) are measured. For example, the expression of genes which are up- or down-regulated in response to a rp-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected.

Exemplary cell lines may include non-recombinant monocyte cell lines, such as U937 (ATCC# CRL-1593), THP-1 (ATCC# TIB-202), and P388D1 (ATCC# TIB-63); endothelial cells such as HUVEC's and bovine aortic endothelial cells (BAEC's); as well as generic mammalian cell lines such as HeLa cells and COS cells, e.g., COS-7 (ATCC# CRL-1651). Further, the transgenic animals discussed herein may be used to generate cell lines, containing one or more cell types involved in cardiovascular disease, that can be used as cell culture. models for this disorder. While primary cultures derived from the cardiovascular disease transgenic animals of the invention may be utilized, the generation of continuous cell lines is preferred. For examples of techniques which may be used to derive a continuous cell line from the transgenic animals, see Small et al., 1985, Mol. Cell Biol. 5:642–648.

For example, the effect of a test compound on a variety of end points could be tested including rates of LDL uptake, adhesion to endothelial cells, transmigration, foam cell formation, fatty streak formation, and production by foam cells of growth factors such as bFGF, IGF-I, VEGF, IL-1, M-CSF, TGFβ, TGFα, TNFα, HB-EGF, PDGF, IFN-γ, and GM-CSF. Similarly, HUVEC's can be treated with test compounds or transfected with genetically engineered rp genes. The HUVEC's can then be examined for phenotypes associated with cardiovascular disease, including, but not limited to changes in cellular morphology, cell proliferation, cell migration, and mononuclear cell adhesion; or for the effects on production of other proteins involved in cardiovascular disease such as ICAM, VCAM, PDGF-β, and E-selectin.

In the event that the rp proteins themselves, or in complexes with other proteins, are capable of binding DNA and modifying transcription of a gene, a transcriptional based assay could be used, for example, in which a rp responsive regulatory sequence is operably linked to a detectable marker gene.

Monitoring the influence of compounds on cells may be applied not only in basic drug screening, but also in clinical trials. In such clinical trials, the expression of a panel of genes may be used as a "read out" of a particular drug's therapeutic effect.

In yet another aspect of the invention, the subject rp polypeptides can be used to generate a "two hybrid" assay (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), for isolating coding sequences for other cellular proteins which bind to or interact with rp ("rp-binding proteins" or "rp-bp"), such as FCHD 534, and the like. Such rp-binding proteins would likely also be involved in the propagation of TGFβ signals by the rp proteins as, for example, the upstream or downstream elements of the rp pathway or as collateral regulators of signal bioactivity.

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a rp polypeptide. The second hybrid protein encodes a transcriptional activation domain fused in frame to a sample gene from a cDNA library. If the bait and sample hybrid proteins are able to interact, e.g., form a rp-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the rp and sample proteins.

4.8 Transgenic Animals

These systems may be used in a variety of applications. For example, the cell- and animal-based model systems may be used to further characterize rp genes and proteins. In addition, such assays may be utilized as part of screening strategies designed to identify compounds which are capable of ameliorating disease symptoms. Thus, the animal- and cell-based models may be used to identify drugs, pharmaceuticals, therapies and interventions which may be effective in treating disease.

4.8.1. Animal-based Systems

One aspect of the present invention concerns transgenic animals which are comprised of cells (of that animal) which contain a transgene of the present invention and which preferably (though optionally) express an exogenous rp protein in one or more cells in the animal. A rp transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a rp protein can be essential for many forms of lineage analysis and can additionally provide a means to assess the effects of, for example, lack of rp expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase, The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject rp proteins. For example, excision of a target sequence which interferes with the expression of a recombinant rp gene, such as one which encodes an antagonistic homolog or an antisense transcript, can be designed to activate expression of that gene. This interference with expression of the protein can result from a variety of mechanisms, such as spatial separation of the rp gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the crelloxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant rp protein can be regulated via control of recombinase expression.

Use of the cre/loxP recombinase system to regulate expression of a recombinant rp protein requires the construction of a transgenic animal containing transgenes encoding both the Cre recombinase and the subject protein. Animals containing both the Cre recombinase and a recombinant rp gene can be provided through the construction of "double" transgenic animals. A convenient method for providing such animals is to mate two transgenic animals each containing a transgene, e.g., a rp gene and recombinase gene.

One advantage derived from initially constructing transgenic animals containing a rp transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic rp transgene is silent will allow the study of progeny from that founder in which disruption of rp mediated induction in a particular tissue or at certain developmental stages would result in, for example, a lethal phenotype.

Similar conditional transgenes can be provided using prokaryotic promoter sequences which require prokaryotic proteins to be simultaneously expressed in order to facilitate expression of the rp transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a rp transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pionuclei are well separated and both are located close to the cell membrane. Alternatively, the e xogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which, nables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels; of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgernic and/or a knockout; where it is transgenic, it may contain the same or a different transgene, or both. Alternatively, the partner may be a parental line. Where in vitro fertilization is used. the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a rp protein (either agonistic or antagonistic), and antisense transcript, or a rp mutant. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927–6931; Van der Putten et al. (1985) PNAS 82:6148–6152). Transfection is easily and efficiently obtained by culturing the blastomeres on a monolayer of virus-producing cells (Van der Putten, supra; Stewart et al. (1987) EMBO J. 6:383–388). Alternatively, infection can be performed at a later stage. Virus or virus-producing cells can be injected into the blastocoele (Jahner et al. (1982) Nature 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) suipra).

A third type of target cell for transgene introduction is the embryonal stem cell (ES). ES cells are obtained from pre-implantation embryos cultured in vitro and fused with embryos (Evans et al. (1981) Nature 292:154–156; Bradley et al. (1984) Nature 309:255–258; Gossler et al. (1986) PNAS 83: 9065–9069; and Robertson et al. (1986) Nature 322:445–448). Transgenes can be efficiently introduced into the ES cells by DNA transfection or by retrovirus-mediatecl transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468–1474.

In one embodiment, gene targeting, which is a method of using homologous recombination to modify an animal's genome, can be used to introduce changes into cultured embryonic stem cells. By targeting a rp gene of interest in ES cells, these changes can be introduced into the germlines of animals to generate chimeras. The gene targeting procedure is accomplished by introducing into tissue culture cells a DNA targeting construct that includes a segment homologous to a target rp locus, and which also includes an intended sequence modification to the rp genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a rp gene function through the use of a targeting transgene construct designed to undergo homologous recombination with one or more rp genomic sequences. The targeting construct can be arranged so that, upon recombination with an element of a rp gene, a positive selection marker is inserted into (or replaces) coding sequences of the targeted siganlin gene. The inserted sequence functionally disrupts the rp gene, while also providing a positive selection trait. Exemplary rp targeting constructs are described in more detail below.

Generally, the embryonic stem cells (ES cells ) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) J. Embryol. Exp. Morphol. 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) PNAS 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) Current. Topics in Devel. Biol. 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, for example, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contpemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the rp coding sequence, transcriptional regulatory sequence, etc. Typically, less than about 1–5% of the ES cells that take up the knockout construct will actually integrate the knockout construct in the desired location. To identify those ES cells with proper integration of the knockout construct, total DNA can be eptracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryoll that are at the proper stage of development to permit integration of the foreign ES cell containing the knockout construct into the developing embryo. For instance, as the appended Examples describe, the transformed ES cells can be microinjected into blastocytes.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While many embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the rp gene knocked out in various tissues of the offspring by probing the Western blot with an antibody against the particular rp protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a rp-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989loning, Volunes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hamnes & S. J. Higgins eds. 1984); *Transcription And Translation* (B. D. Hames & S. J. Higgins eds. 1984); *Culture of Animal Cells* (R. I. Freshney, Alan R. Liss, Inc., 1987); *Immobiized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Cals eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLE 1

Identiification and Characterization of a Human rp Gene Fragment

The mouse tub gene nucleotide sequence was utilized as a database query using the Blastx program (1993, Nature Genetics 3:266–272), which resulted in the identification of a human EST (GenBank Accession No. H92408) which exhibited a 75.3% identity over 85 derived amino acid residues. The EST was originally derived from a human retinal library (Soares, B. and Benaldo, F. Washington University-Merck EST Project, Washington University School of Medicine, St. Louis, Mo.).

Upon identification of the EST, the corresponding clone, Acc. No. H92408, was obtained from Research Genetics, Inc (Huntsville, Alabama) and sequenced. A number of errors in the sequence listed in the database were found. These included a deletion of bp 33 from the Genbank sequence, incorrect base pair insertions (Genbank sequence bps 330, 339, 359, 366, 375 and 384), incorrect sequence at bps 133–137 (ACCGA in Genbank sequence, as opposed to the correct GGCCG sequence) and incorrect bp 398 (T in Genbank as opposed to the correct G). The identified sequence was used to screen a retinal cDNA library, which resulted in the identification of several positive clones.

FIG. 2 shows the nucleotide and deduced amino acid sequence of the hrp fragment identified via this screening effort. The sequence exhibits a 73.9% identity with htub over 216 derived amino acid residues. Full-length htub is comprised of 506 amino acids. The clone was then used to isolate further cDNAs encompassing the whole open reading frame as described in Example 2.

The EST derived from hrp was mapped in the human by PCR typing of the Genebridge (G4) radiation hybrid panel. Typing of the DNA and comparison to radiation hybrid map data at the Whitehead Institute Center for Genome Research (WICGR) tightly linked the EST to an anonymous STS, WI-4186, on human chromosome 6. Additionally, the EST was genetically mapped in the mouse using a C57BL/6J× Mus spretus interspecific backcross. Genotyping of 100 meioses demonstrated linkage to a region on mouse chromosome 17 between D17Mit48 and D7Mit 9.

Human multiple tissue northern blots (Cat. No. 7766-1 and 7760-1; Clonetech, Palo Alto Calif.) containing 2 μg of poly A+RNA per lane were probed with the approximately 1.35 kb EcoRI-NotI fragment of the sequence obtained from Genbank containing the hrp insert shown in FIG. 2. The filters were prehybridized in 5 mls of Church buffer at 65° C. for 1 hour, after which 100 ng of $^{32}$P-labelled probe was added. Probe was made using Stratagene Prime-It kit (Cat. No. 300392; Stratagene, La Jolla Calif.). Hybridization was allowed to proceed at 65° C. for approximately 18 hours. Final washes of the filters was in 0.1% SDS, 0.2×SSC solution for 65° C. Washed filters were exposed to a phosphoimager for 4 hours. Tissues tested included brain, lung, liver, kidney, spleen, thymus, m8uscle, prostate, testis and fat.

A message of approximately 2 kb was apparent in the lanes containing RNA from skeletal muscle and testis.

EXAMPLE 2

Identification and Characterization of a Full Length Human rp Gene hrp Mapping.

PCR primers—h92408 forward —CGTGGAGGTGGACGAACC (SEQ ID NO 12 and reverse —CC(GTGTCCAGGTGCAGGA (SEQ ID NO 13) were first tested on human and hamster genomic DNA for specific amplification. Each PCR reaction consisted of: 5 μl (50 ng) genomic DNA, 2 μl primers (10 μM each), 2 μl 10×PCR buffer (15 mM MgC12, 100 mM Tris-HCl 500 mM KCl Perkin Elmer), 1 u Taq polymerase (5 u/μl Perkin Elmer), and 10.8 μl diH20. Reactions were thermocycled on a Perkin Elmer 9600 for 94° C. 3 minutes, [94° C. 30 sec, 55° C. 30 sec., 72° C., 30 sec.] 35X, 72° C. 7 minutes, 4° C. hold. Resulting PCR products were run out on a 2% agarose gel, and visualised on a UV light box. The primers specifically amplified a 150 bp product from human genomic DNA, but no product from hamster genomic DNA.

Radiation Hybrid Mapping of hrp

PCR reactions of radiation hybrid panels, GeneBridge 4 and Stanford G3 (Research Genetics), were assembled in duplicate using an automated PCR assembly progam on a TECAN Genesis. Each reaction consisted of: 10 μl hybrid DNA (5 ng/μl), 2 μl primers (10 μM each), and 8 μl PCR cocktail (final concentrations: 1.5 mM MgCl2, 10 mM Tris-HCl, 50 mM KCl, 1 u Taq polymerase). The reactions were thermocycled on a Perkin Elmer 9600 for 94° C. 3 minutes, [94° C. 30 sec, 55° C. 30 sec, 72° C., 30 sec] 35X, 72° C. 7 minutes, 4° C. hold. Resulting PCR products were run out on a 2% agarose gel, and visualized on a UV light box.

Positive hybrids for the Genebridge 4 panel were: 1, 8, 13, 18, 22, 26, 31, 32, 34, 36, 38, 43, 46, 49, 51, 53, 54, 60, 62, 63, 65, 69, 73, 74, 78, 79, 82, and 84. These data were submitted to the Whitehead Genome Center for placement in relation to a framework map. The placement results mapped the tub-homolog to chromosome 6, 0.00cR from Whitehead framework marker WI-4186, with a LOD score >3.0.

Positive hybrids for the Stanford G3 panel were: 8, 9, 14, 16, 27, 29, 49, 62, 64, 66, 67, 68, 72, 81, and 83. These data were submitted to the Stanford Genome Center Radiation Hybrid mapping server for 2 point analysis and placement in relation to a framework map. This resulted in mapping hrp to chromosome 6, 31.22 cR from Stanford framework marker D6S291, with a LOD score of 7.7.

Northern Analysis

Human Tissue

Human multiple tissue northern blots, MTNB, Cat #7766-1 and 7760-1 (Clonetech, Palo Alto, Calif.), containing 2 μg of poly A+RNA per lane were probed with approximately 1.35 kb EcoR1-Not 1 fragment of ATCC 98147 containing hrp. The filters were prehybridized in 5 ml of Church buffer at 65° C. for 1 hour, after which 100 ng of 32-P labelled probe was added. Probe was made using the Stratagene Prime-It kit, Cat. #300392 (Clonetech, Palo Alto, Calif.). Hybridization was allowed to proceed at 65° C. for approximately 18 hours. Final washes of the filters was in 0.1% SDS, 0.2×SSC solution at 65° C. The filters were then exposed to the phosphoimager for 4 h6urs. The human tissues tested included: spleen, thymus, prostate, testes, uterus, small intestine, colon, peripheral blood leukocytes, heart, brain, placenta, lung, liver, skeletal muscle, kidney, pancreas and retina.

A band of approximately 2 kb indicating the detection of hrp was apparent in the lanes containing RNA from skeletal muscle and testis. A major band of approximately 2 kb appeared in the lane containing RNA from retina, as well as minor bands of 3.0, 3.5, 4.4, 5.0 and 7.5. No band corresponding to htub was detected.

Cell Lines

Poly A+RNA was isolated from a variety of ATCC cell lines (including human neuroblastoma cell lines SKNMC, SKNJH, NB412A, Neuro2A, HTB10, HTB22, CRL1658, HTB11, CCL147, CCL131; and the human breast carcinoma cell line MCF7 and he mouse fibroblast cell line NIH 3T3) were probed with the approximately 1.35 kb EcoRI-NotI fragment of the sequence obtained from Genbank containing the hrp insert shown in FIG. 2 using the Fast Track System (Invitrogen, San Diego, Calif.).

A very veak band of approximately 7 kb indicating the detection of hrp was pparent in the lane containing RNA from the human neuroblastom cell line Neuro2A.

EXAMPLE 3

Hybridization of the Full Length Human rp Gene to Htub

Human and mouse cDNA or genomic libraries are hybridized with 1.35 kb EcoR1-Not 1 fragment of ATCC 98147 under standard conditions (0.5M NaHPO$_4$, 7% dodecyl sulfate (SDS), 1 mM EDTA at 65° C. The mixture is subsequently washed at a high stringency of 0.1×SSC/1% SDS/68° C./30 min.

Hrp Transcripts are Detected, but not htub or mtub.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. An isolated nucleic acid molecule encoding the amino acid sequence of SEQ ID NO:2, or a full complement thereof.

2. An isolated nucleic acid molecule comprising the nucleotide sequence of SEQ ID NO:1, or a full complement thereof.

3. An isolated nucleic acid molecule comprising the nucleotide sequence of SEQ ID NO:3, or a full complement thereof.

4. An isolated nucleic acid molecule comprising the nucleotide sequence of the DNA insert of the plasmid deposited with American Type Culture Collection as Accession Number 98144, or a full complement thereof.

5. An isolated nucleic acid molecule comprising the nucleotide sequence of the DNA insert of the plasmid deposited with American Type Culture Collection as Accession Number 98147, or a full complement thereof.

6. An isolated nucleic acid molecule encoding the amino acid sequence of SEQ ID NO:5, or a full complement thereof.

7. An isolated nucleic acid molecule comprising the nucleotide sequence of SEQ ID NO:6, or a full complement thereof.

8. A vector comprising the nucleic acid molecule of any one of claims 1, 2, 3, 4, 5, 6, or 7.

9. An isolated nucleic, acid molecule comprising the nucleic acid molecule of any one of claims 1, 2, 3, 4, 5, 6 or 7 and a nucleic acid sequence encoding a heterologous polypeptide.

10. An isolated host-cell which is transfected with the nucleic acid molecule of any one of claims 1, 2, 3, 4, 5, 6 or 7.

11. The host cell of claim 10 which is a mammalian host cell.

12. A method for expressing a polypeptide comprising culturing the isolated host cell of claim 11 under conditions in which the nucleic acid molecule is expressed, thereby expressing said polypeptide.

13. A kit comprising a nucleic acid molecule of any one of claims 1, 2, 3, 4, 5, 6 or 7 and instructions for use.

14. A composition comprising the nucleic acid molecule of any one of claims 1, 2, 3, 4, 5, 6 or 7.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 2184 base pairs
      (B) TYPE: nucleic acid
      (C) STRANDEDNESS: single
      (D) TOPOLOGY: linear (ii) MOLECULE TYPE: cDNA -continued (ix) FEATURE:
  (A) NAME/KEY: CDS
  (B) LOCATION: 569..1616

(xi) SEQUENCE DESCRIPTION: SEQ ID NO:1:

```
GAATTCCGGG AAGCTGAATG GAAGCCGGGG AGAAGTGTTG AAAGTGGAAA C CCAAGCCCA      60

GGGGAGATCC CTAGGGTGAG GAGCCCGAGG GGGTGCGCCC AGGCTTGGGG G TAGCGGGTA     120

GAGGCGCTGC CTCGCGGACC CGCGGATGGG ACCCTGTCTG AACCCCGCAT C TCGGCTCAG     180

CTGGGCGGAG GGGGAGGCCG CGGGAGGAGC CTTCCCCAGA CCCAGCCCAG G CCCGGCGC      240

CGCAGACGGT CTACGCCAGG TTCCTCAGGG ACCCCGAGGC CAAGAAGCGC G ACCCCCGGG     300

AAACCTTTCT GGTAGCCCGT GCCCCAGACG CGGAGGACGA GGAGGAGGAG G AAGAGGAGG     360

ACGAGGAGGA CGAAGAAGAT GAGCMGARGA AAAGAAAGAG AAAATCCTTC T GCCTCCCAA     420

GAARCCCCTG AGAGAGAAGA GCTCCGCAGA CCTGAANGAN AAGAAGGCCA A NGCCCASGG     480

CCCAAGGGGA GACCTGGGAA GCCCTGACCC CCCACCGAAA CCTCTGCGTG T TAGGAATAA     540

GGAAGCTCCA GCAGGGGAGG GGACCAAG ATG AGA AAG ACC AAG  AAG AAA GGG         592
                                Met Arg Lys Thr Lys  Lys Lys Gly
                                 1               5
```

```
TCT GGG GAG GCC GAC AAG GAC CCC TCA GGG A GC CCA GCC AGT GCG AGG        640
Ser Gly Glu Ala Asp Lys Asp Pro Ser Gly S er Pro Ala Ser Ala Arg
 10              15                  20

AAG AGC CCA GCA GCC ATG TTT CTG GTT GGG G AA GGC AGT CCT GAC AAG        688
Lys Ser Pro Ala Ala Met Phe Leu Val Gly G lu Gly Ser Pro Asp Lys
 25              30                  35                  40

AAA GCC CTG AAG AAG AAA GGC ACT CCC AAA G GC GCG AGG AAG GAG GAA        736
Lys Ala Leu Lys Lys Lys Gly Thr Pro Lys G ly Ala Arg Lys Glu Glu
                 45                  50                  55

GAA GAG GAG GAG GAG GCA GCT ACG GTG ACA A AG AAC AGC AAT CAA AAG        784
Glu Glu Glu Glu Glu Ala Ala Thr Val Thr L ys Asn Ser Asn Gln Lys
         60                  65                  70

GGC AAA GCC AAA GGA AAA GGC AAA AAG AAA G CG AAG GAG GAG AGG GCC        832
Gly Lys Ala Lys Gly Lys Gly Lys Lys Lys A la Lys Glu Glu Arg Ala
         75                  80                  85

CCG TCT CCC CCC GTG GAG GTG GAC GAA CCC C GG GAG TTT GTG TTC CGG        880
Pro Ser Pro Pro Val Glu Val Asp Glu Pro A rg Glu Phe Val Phe Arg
 90                  95                  100

CCT GCC CCC CAG GGC CGC ACG GTG CGC TGC C GG CTG ACC CGG GAC AAA        928
Pro Ala Pro Gln Gly Arg Thr Val Arg Cys A rg Leu Thr Arg Asp Lys
105             110                 115                  120

AAG GGC ATG GAT CGA GGC ATG TAT CCC TCC T AC TTC CTG CAC CTG GAC        976
Lys Gly Met Asp Arg Gly Met Tyr Pro Ser T yr Phe Leu His Leu Asp
                 125                 130                  135

ACG GAG AAG AAG GTG TTC CTC TTG GCT GGC A GG AAA CGA AAA CGG AGC       1024
Thr Glu Lys Lys Val Phe Leu Leu Ala Gly A rg Lys Arg Lys Arg Ser
         140                 145                  150

AAG ACA GCC AAT TAC CTC ATC TCC ATC GAC C CT ACC AAT CTG TCC CGA       1072
Lys Thr Ala Asn Tyr Leu Ile Ser Ile Asp P ro Thr Asn Leu Ser Arg
         155                 160                  165

GGA GGG GAG AAT TTC ATC GGG AAG CTG AGG T CC AAC CTC CTG GGG AAC       1120
Gly Gly Glu Asn Phe Ile Gly Lys Leu Arg S er Asn Leu Leu Gly Asn
170                 175                  180

CGC TTC ACG GTC TTT GAC AAC GGG CAG AAC C CA CAG CGT GGG TAC AGC       1168
Arg Phe Thr Val Phe Asp Asn Gly Gln Asn P ro Gln Arg Gly Tyr Ser
185             190                 195                  200

ACT AAT GTG GCA AGC CTT CGG CAG GAG CTG G CA GCT GTG ATC TAT GAA       1216
Thr Asn Val Ala Ser Leu Arg Gln Glu Leu A la Ala Val Ile Tyr Glu
                 205                 210                  215
```

-continued

```
ACC AAC GTG CTG GGC TTC CGT GGC CCC CGG C GC ATG ACC GTC ATC ATT       1264
Thr Asn Val Leu Gly Phe Arg Gly Pro Arg A rg Met Thr Val Ile Ile
            220                 225                 230

CCT GGC ATG AGT GCG GAG AAC GAG AGG GTC C CC ATC CGG CCC CGA AAT       1312
Pro Gly Met Ser Ala Glu Asn Glu Arg Val P ro Ile Arg Pro Arg Asn
                235                 240                 245

GCT AGT GAC GGC CTG CTG GTG CGC TGG CAG A AC AAG ACG CTG GAG AGC       1360
Ala Ser Asp Gly Leu Leu Val Arg Trp Gln A sn Lys Thr Leu Glu Ser
    250                 255                 260

CTC ATA GAA CTG CAC AAC AAG CCA CCT GTC T GG AAC GAT GAC AGT GGC       1408
Leu Ile Glu Leu His Asn Lys Pro Pro Val T rp Asn Asp Asp Ser Gly
265                 270                 275                 280

TCC TAC ACC CTC AAC TTC CAA GGC CGG GTC A CC CAG GCC TCA GTC AAG       1456
Ser Tyr Thr Leu Asn Phe Gln Gly Arg Val T hr Gln Ala Ser Val Lys
                285                 290                 295

AAC TTC CAG ATT GTC CAC GCT GAT GAC CCC G AC TAT ATC GTG CTG CAG       1504
Asn Phe Gln Ile Val His Ala Asp Asp Pro A sp Tyr Ile Val Leu Gln
                    300                 305                 310

TTC GGC CGC GTG GCG GAG GAC GCC TTC ACC C TA GAC TAC CGG TAC CCG       1552
Phe Gly Arg Val Ala Glu Asp Ala Phe Thr L eu Asp Tyr Arg Tyr Pro
                315                 320                 325

CTG TGC GCC CTG CAG GCC TTC GCC ATC GCC C TC TCC AGT TTC GAC GGG       1600
Leu Cys Ala Leu Gln Ala Phe Ala Ile Ala L eu Ser Ser Phe Asp Gly
    330                 335                 340

AAG CTG GCC TGC GAG T GACCCCAGCA GCCCCTCAGC GCC CCCAGAG CCCGTCAGCG     1656
Lys Leu Ala Cys Glu
345

TGGGGGAAAG GATTCAGTGG AGGCTGGCAG GGTCCCTCCA GCAAAGCTCC C GCGGAAAAC    1716

TGCTCCTGTG TCGGGCTGA CCTCTCACTG CCTCTCGGTG ACCTCCGTCC T CTCCCCAGC    1776

CTGGCACAGG CCGAGGCAGG AGGAGCCCGG ACGGCGGGTA GGACGGAGAT G AAGAACATC    1836

TGGAGTTGGA GCCGCACATC TGGTCTCGGA GCTCGCCTGC GCCGCTGTGC C CCCCTCCTC    1896

CCCGCGCCCC AGTCACTTCC TGTCCGGGAG CAGTAGTCAG TGTTGTTTTA A CCTCCCCTC    1956

TCCCCGGGAC CGCGCTAGGG CTCCGAGGAG CTGGGGCGGG CTAGGAGGAG G GGGTAGGTG    2016

ATGGGGGACG AGGGCCAGGC ACCCACATCC CCAATAAAGC CGCGTCCTTG G CMAAAAAA     2076

AAAAAAAAAA AAAAAAAAAA AAAAAAAAAA AAAAAAAAAA AAAAAAAAAA A AAAAAAAA    2136

AAAAAAAAAA AAAAAAAAAA AAAAAAAAAA AAAAAAAAC CGGAATTC                  2184
```

(2) INFORMATION FOR SEQ ID NO:2:

(i) SEQUENCE CHARACTERISTICS:
        (A) LENGTH: 349 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Lys Thr Lys Lys Gly Ser Gly G lu Ala Asp Lys Asp Pro
  1               5                  10                  15

Ser Gly Ser Pro Ala Ser Ala Arg Lys Ser P ro Ala Ala Met Phe Leu
                20                  25                  30

Val Gly Glu Gly Ser Pro Asp Lys Lys Ala L eu Lys Lys Lys Gly Thr
            35                  40                  45

Pro Lys Gly Ala Arg Lys Glu Glu Glu G lu Glu Glu Ala Ala Thr
    50                  55                  60
```

```
Val Thr Lys Asn Ser Asn Gln Lys Gly Lys Ala Lys Gly Lys Gly Lys
 65                  70                  75                  80

Lys Lys Ala Lys Glu Glu Arg Ala Pro Ser Pro Pro Val Glu Val Asp
                 85                  90                  95

Glu Pro Arg Glu Phe Val Phe Arg Pro Ala Pro Gln Gly Arg Thr Val
            100                 105                 110

Arg Cys Arg Leu Thr Arg Asp Lys Lys Gly Met Asp Arg Gly Met Tyr
            115                 120                 125

Pro Ser Tyr Phe Leu His Leu Asp Thr Glu Lys Lys Val Phe Leu Leu
            130                 135                 140

Ala Gly Arg Lys Arg Lys Arg Ser Lys Thr Ala Asn Tyr Leu Ile Ser
145                 150                 155                 160

Ile Asp Pro Thr Asn Leu Ser Arg Gly Gly Glu Asn Phe Ile Gly Lys
                165                 170                 175

Leu Arg Ser Asn Leu Leu Gly Asn Arg Phe Thr Val Phe Asp Asn Gly
                180                 185                 190

Gln Asn Pro Gln Arg Gly Tyr Ser Thr Asn Val Ala Ser Leu Arg Gln
                195                 200                 205

Glu Leu Ala Ala Val Ile Tyr Glu Thr Asn Val Leu Gly Phe Arg Gly
            210                 215                 220

Pro Arg Arg Met Thr Val Ile Ile Pro Gly Met Ser Ala Glu Asn Glu
225                 230                 235                 240

Arg Val Pro Ile Arg Pro Arg Asn Ala Ser Asp Gly Leu Leu Val Arg
                245                 250                 255

Trp Gln Asn Lys Thr Leu Glu Ser Leu Ile Glu Leu His Asn Lys Pro
                260                 265                 270

Pro Val Trp Asn Asp Asp Ser Gly Ser Tyr Thr Leu Asn Phe Gln Gly
                275                 280                 285

Arg Val Thr Gln Ala Ser Val Lys Asn Phe Gln Ile Val His Ala Asp
            290                 295                 300

Asp Pro Asp Tyr Ile Val Leu Gln Phe Gly Arg Val Ala Glu Asp Ala
305                 310                 315                 320

Phe Thr Leu Asp Tyr Arg Tyr Pro Leu Cys Ala Leu Gln Ala Phe Ala
                325                 330                 335

Ile Ala Leu Ser Ser Phe Asp Gly Lys Leu Ala Cys Glu
                340                 345

(2) INFORMATION FOR SEQ ID NO:3:

(i) SEQUENCE CHARACTERISTICS:
        (A) LENGTH: 1047 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1047

(xi) SEQUENCE DESCRIPTION: SEQ ID NO:3:

ATG AGA AAG ACC AAG AAG AAA GGG TCT GGG GAG GCC GAC AAG GAC CCC      48
Met Arg Lys Thr Lys Lys Lys Gly Ser Gly Glu Ala Asp Lys Asp Pro
  1               5                  10                  15

TCA GGG AGC CCA GCC AGT GCG AGG AAG AGC CCA GCA GCC ATG TTT CTG      96
Ser Gly Ser Pro Ala Ser Ala Arg Lys Ser Pro Ala Ala Met Phe Leu
             20                  25                  30
```

```
GTT GGG GAA GGC AGT CCT GAC AAG AAA GCC C TG AAG AAG AAA GGC ACT        144
Val Gly Glu Gly Ser Pro Asp Lys Lys Ala L eu Lys Lys Lys Gly Thr
        35              40                  45

CCC AAA GGC GCG AGG AAG GAG GAA GAG G AG GAG GAG GCA GCT ACG            192
Pro Lys Gly Ala Arg Lys Glu Glu Glu G lu Glu Glu Ala Ala Thr
    50              55                  60

GTG ACA AAG AAC AGC AAT CAA AAG GGC AAA G CC AAA GGA AAA GGC AAA        240
Val Thr Lys Asn Ser Asn Gln Lys Gly Lys A la Lys Gly Lys Gly Lys
65              70                  75                  80

AAG AAA GCG AAG GAG GAG AGG GCC CCG TCT C CC CCC GTG GAG GTG GAC        288
Lys Lys Ala Lys Glu Glu Arg Ala Pro Ser P ro Pro Val Glu Val Asp
                    85                  90                  95

GAA CCC CGG GAG TTT GTG TTC CGG CCT GCC C CC CAG GGC CGC ACG GTG        336
Glu Pro Arg Glu Phe Val Phe Arg Pro Ala P ro Gln Gly Arg Thr Val
                100                 105                 110

CGC TGC CGG CTG ACC CGG GAC AAA AAG GGC A TG GAT CGA GGC ATG TAT        384
Arg Cys Arg Leu Thr Arg Asp Lys Lys Gly M et Asp Arg Gly Met Tyr
            115                 120                 125

CCC TCC TAC TTC CTG CAC CTG GAC ACG GAG A AG AAG GTG TTC CTC TTG        432
Pro Ser Tyr Phe Leu His Leu Asp Thr Glu L ys Lys Val Phe Leu Leu
    130                 135                 140

GCT GGC AGG AAA CGA AAA CGG AGC AAG ACA G CC AAT TAC CTC ATC TCC        480
Ala Gly Arg Lys Arg Lys Arg Ser Lys Thr A la Asn Tyr Leu Ile Ser
145                 150                 155                 160

ATC GAC CCT ACC AAT CTG TCC CGA GGA GGG G AG AAT TTC ATC GGG AAG        528
Ile Asp Pro Thr Asn Leu Ser Arg Gly Gly G lu Asn Phe Ile Gly Lys
                165                 170                 175

CTG AGG TCC AAC CTC CTG GGG AAC CGC TTC A CG GTC TTT GAC AAC GGG        576
Leu Arg Ser Asn Leu Leu Gly Asn Arg Phe T hr Val Phe Asp Asn Gly
            180                 185                 190

CAG AAC CCA CAG CGT GGG TAC AGC ACT AAT G TG GCA AGC CTT CGG CAG        624
Gln Asn Pro Gln Arg Gly Tyr Ser Thr Asn V al Ala Ser Leu Arg Gln
    195                 200                 205

GAG CTG GCA GCT GTG ATC TAT GAA ACC AAC G TG CTG GGC TTC CGT GGC        672
Glu Leu Ala Ala Val Ile Tyr Glu Thr Asn V al Leu Gly Phe Arg Gly
210                 215                 220

CCC CGG CGC ATG ACC GTC ATC ATT CCT GGC A TG AGT GCG GAG AAC GAG        720
Pro Arg Arg Met Thr Val Ile Ile Pro Gly M et Ser Ala Glu Asn Glu
225                 230                 235                 240

AGG GTC CCC ATC CGG CCC CGA AAT GCT AGT G AC GGC CTG CTG GTG CGC        768
Arg Val Pro Ile Arg Pro Arg Asn Ala Ser A sp Gly Leu Leu Val Arg
                245                 250                 255

TGG CAG AAC AAG ACG CTG GAG AGC CTC ATA G AA CTG CAC AAC AAG CCA        816
Trp Gln Asn Lys Thr Leu Glu Ser Leu Ile G lu Leu His Asn Lys Pro
            260                 265                 270

CCT GTC TGG AAC GAT GAC AGT GGC TCC TAC A CC CTC AAC TTC CAA GGC        864
Pro Val Trp Asn Asp Asp Ser Gly Ser Tyr T hr Leu Asn Phe Gln Gly
    275                 280                 285

CGG GTC ACC CAG GCC TCA GTC AAG AAC TTC C AG ATT GTC CAC GCT GAT        912
Arg Val Thr Gln Ala Ser Val Lys Asn Phe G ln Ile Val His Ala Asp
290                 295                 300

GAC CCC GAC TAT ATC GTG CTG CAG TTC GGC C GC GTG GCG GAG GAC GCC        960
Asp Pro Asp Tyr Ile Val Leu Gln Phe Gly A rg Val Ala Glu Asp Ala
305                 310                 315                 320

TTC ACC CTA GAC TAC CGG TAC CCG CTG TGC G CC CTG CAG GCC TTC GCC       1008
Phe Thr Leu Asp Tyr Arg Tyr Pro Leu Cys A la Leu Gln Ala Phe Ala
                325                 330                 335

ATC GCC CTC TCC AGT TTC GAC GGG AAG CTG G CC TGC GAG                   1047
Ile Ala Leu Ser Ser Phe Asp Gly Lys Leu A la Cys Glu
            340                 345
```

(2) INFORMATION FOR SEQ ID NO:4:

(i) SEQUENCE CHARACTERISTICS:
        (A) LENGTH: 1338 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..858

(xi) SEQUENCE DESCRIPTION: SEQ ID NO:4:

```
GTG ATA AAG AAC AGC AAT CAA AAG GGC AAA G CC AAA GGA AAA GGC AAA       48
Val Ile Lys Asn Ser Asn Gln Lys Gly Lys A la Lys Gly Lys Gly Lys
 1               5                  10                  15

AAG AAA GCG AAG GAG GAG AGG GCC CCG TCT C CC CCC GTG GAG GTG GAC       96
Lys Lys Ala Lys Glu Glu Arg Ala Pro Ser P ro Pro Val Glu Val Asp
            20                  25                  30

GAA CCC CGG GAG TTT GTG CTC CGG CCT GCC C CC CAG GGC CGC ACG GTG      144
Glu Pro Arg Glu Phe Val Leu Arg Pro Ala P ro Gln Gly Arg Thr Val
        35                  40                  45

CGC TGC CGG CTG ACC CGG GAC AAA AAG GGC A TG GAT CGA GGC ATG TAT      192
Arg Cys Arg Leu Thr Arg Asp Lys Lys Gly M et Asp Arg Gly Met Tyr
    50                  55                  60

CCC TCC TAC TTC CTG CAC CTG GAC ACG GAG A AG AAG GTG TTC CTC TTG      240
Pro Ser Tyr Phe Leu His Leu Asp Thr Glu L ys Lys Val Phe Leu Leu
65                  70                  75                  80

GCT GGC AGG AAA CGA AAA CGG AGC AAG ACA G CC AAT TAC CTC ATC TCC      288
Ala Gly Arg Lys Arg Lys Arg Ser Lys Thr A la Asn Tyr Leu Ile Ser
                85                  90                  95

ATC GAC CCT ACC AAT CTG TCC CGA GGA GGG G AG AAT TTC ATC GGG AAG      336
Ile Asp Pro Thr Asn Leu Ser Arg Gly Gly G lu Asn Phe Ile Gly Lys
            100                 105                 110

CTG AGG TCC AAC CTC CTG GGG AAC CGC TTC A CG GTC TTT GAC AAC GGG      384
Leu Arg Ser Asn Leu Leu Gly Asn Arg Phe T hr Val Phe Asp Asn Gly
        115                 120                 125

CAG AAC CCA CAG CGT GGG TAC AGC ACT AAT G TG GCA AGC CTT CGG CAG      432
Gln Asn Pro Gln Arg Gly Tyr Ser Thr Asn V al Ala Ser Leu Arg Gln
    130                 135                 140

GAG CTG GCA GCT GTG ATC TAT GAA ACC AAC G TG CTG GGC TTC CGT GGC      480
Glu Leu Ala Ala Val Ile Tyr Glu Thr Asn V al Leu Gly Phe Arg Gly
145                 150                 155                 160

CCC CGG CGC ATG ACC GTC ATC ATT CCT GGC A TG AGT GCG GAG AAC GAG      528
Pro Arg Arg Met Thr Val Ile Ile Pro Gly M et Ser Ala Glu Asn Glu
                165                 170                 175

AGG GTC CCC ATC CGG CCC CGA AAT GCT AGT G AC GGC CTG CTG GTG CGC      576
Arg Val Pro Ile Arg Pro Arg Asn Ala Ser A sp Gly Leu Leu Val Arg
            180                 185                 190

TGG CAG AAC AAG ACG CTG GAG AGC CTC ATA G AA CTG CAC AAC AAG CCA      624
Trp Gln Asn Lys Thr Leu Glu Ser Leu Ile G lu Leu His Asn Lys Pro
        195                 200                 205

CCT GTC TGG AAC GAT GAC AGT GGC TCC TAC A CC CTC AAC TTC CAA GGC      672
Pro Val Trp Asn Asp Asp Ser Gly Ser Tyr T hr Leu Asn Phe Gln Gly
    210                 215                 220

CGG GTC ACC CAG GCC TCA GTC AAG AAC TTC C AG ATT GTC CAC GCT GAT      720
Arg Val Thr Gln Ala Ser Val Lys Asn Phe G ln Ile Val His Ala Asp
225                 230                 235                 240

GAC CCC GAC TAT ATC GTG CTG CAG TTC GGC C GC GTG GCG GAG GAC GCC      768
Asp Pro Asp Tyr Ile Val Leu Gln Phe Gly A rg Val Ala Glu Asp Ala
                245                 250                 255
```

```
TTC ACC CTA GAC TAC CGG TAC CCG CTG TGC G CC CTG CAG GCC TTC GCC      816
Phe Thr Leu Asp Tyr Arg Tyr Pro Leu Cys A la Leu Gln Ala Phe Ala
            260                 265                 270

ATC GCC CTC TCC AGT TTC GAC GGG AAG CTG G CC TGC GAG TGACCCAGC        865
Ile Ala Leu Ser Ser Phe Asp Gly Lys Leu A la Cys Glu
        275                 280                 285

AGCCCCTCAG CGCCCCAGA GCCCGTCAGC GTGGGGAAA GGATTCAGTG G AGGCTGGCA      925

GGGTCCCTCC AGCAAAGCTC CGCGGAAAA CTGCTCCTGT GTCGGGCTG A CCTCTCACT     985

GCCTCTCGGT GACCTCCGTC CTCTCCCCAG CCTGGCACAG GCCGAGGCAG G AGGAGCCCG  1045

GACGGCGGGT AGGACGGAGA TGAAGAACAT CTGGAGTTGG AGCCGCACAT C TGGTCTCGG  1105

AGCTCGCCTG CGCCGCTGTG CCCCCCTCCT CCCCGCGCCC CAGTCACTTC C TGTCCGGGA  1165

GCAGTAGTCA TTGTTGTTTT AACCTCCCCT CTCCCCGGGA CCGCGCTAGG G CTCCGAGGA  1225

GCTGGGGCGG GCTAGGAGGA GGGGGTAGGT GATGGGGGAC GAGGGCCAGG C ACCCACATC  1285

CCCAATAAAG CCGCGTCCTT GGCAAAAAAA AAAAAAAAAA AAAAAAAAAA A AA         1338
```

(2) INFORMATION FOR SEQ ID NO:5:

(i) SEQUENCE CHARACTERISTICS:
        (A) LENGTH: 285 amino acids
        (B) TYPE: amino acid
        (D) TOPOLOGY: linear (ii) MOLECULE TYPE: protein (xi) SEQUENCE DESCRIPTION: SEQ ID NO:5:

```
Val Ile Lys Asn Ser Asn Gln Lys Gly Lys A la Lys Gly Lys Gly Lys
 1               5                  10                  15

Lys Lys Ala Lys Glu Glu Arg Ala Pro Ser P ro Pro Val Glu Val Asp
            20                  25                  30

Glu Pro Arg Glu Phe Val Leu Arg Pro Ala P ro Gln Gly Arg Thr Val
            35                  40                  45

Arg Cys Arg Leu Thr Arg Asp Lys Lys Gly M et Asp Arg Gly Met Tyr
        50                  55                  60

Pro Ser Tyr Phe Leu His Leu Asp Thr Glu L ys Lys Val Phe Leu Leu
 65                 70                  75                  80

Ala Gly Arg Lys Arg Lys Arg Ser Lys Thr A la Asn Tyr Leu Ile Ser
                85                  90                  95

Ile Asp Pro Thr Asn Leu Ser Arg Gly Gly G lu Asn Phe Ile Gly Lys
                100                 105                 110

Leu Arg Ser Asn Leu Leu Gly Asn Arg Phe T hr Val Phe Asp Asn Gly
            115                 120                 125

Gln Asn Pro Gln Arg Gly Tyr Ser Thr Asn V al Ala Ser Leu Arg Gln
        130                 135                 140

Glu Leu Ala Ala Val Ile Tyr Glu Thr Asn V al Leu Gly Phe Arg Gly
145                 150                 155                 160

Pro Arg Arg Met Thr Val Ile Pro Gly M et Ser Ala Glu Asn Glu
                165                 170                 175

Arg Val Pro Ile Arg Pro Arg Asn Ala Ser A sp Gly Leu Leu Val Arg
            180                 185                 190

Trp Gln Asn Lys Thr Leu Glu Ser Leu Ile G lu Leu His Asn Lys Pro
        195                 200                 205

Pro Val Trp Asn Asp Asp Ser Gly Ser Tyr T hr Leu Asn Phe Gln Gly
    210                 215                 220
```

```
Arg Val Thr Gln Ala Ser Val Lys Asn Phe Gln Ile Val His Ala Asp
225                 230                 235                 240

Asp Pro Asp Tyr Ile Val Leu Gln Phe Gly Arg Val Ala Glu Asp Ala
                245                 250                 255

Phe Thr Leu Asp Tyr Arg Tyr Pro Leu Cys Ala Leu Gln Ala Phe Ala
            260                 265                 270

Ile Ala Leu Ser Ser Phe Asp Gly Lys Leu Ala Cys Glu
        275                 280                 285

(2) INFORMATION FOR SEQ ID NO:6:

(i) SEQUENCE CHARACTERISTICS:
        (A) LENGTH: 1801 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 139..1653

(xi) SEQUENCE DESCRIPTION: SEQ ID NO:6:

CTGCAGGATT CGGCACGAGC AGCGGTCGGG CCGGGGAGGA TGCGGCCCGG G GCGGCCCGA      60

GAGTTGAGCA GGGTCCCCGC GCCAGCCCCG AGCGGTCCCG GCCACCGGAG C CGCAGCCGC    120

CGCCCCGCCC CCGGGAGA ATG ACT TCC AAG CCG CAT TCC  GAC TGG ATT CCT      171
                    Met Thr Ser Lys Pro His Ser  Asp Trp Ile Pro
                      1               5                     10

TAC AGT GTC CTA GAT GAT GAG GGC AGC AAC C TG AGG CAG CAG AAG CTC      219
Tyr Ser Val Leu Asp Asp Glu Gly Ser Asn L eu Arg Gln Gln Lys Leu
                15                  20                  25

GAC CGG CAG CGG GCC CTG TTG GAA CAG AAG C AG AAG AAG AAG CGC CAA      267
Asp Arg Gln Arg Ala Leu Leu Glu Gln Lys G ln Lys Lys Lys Arg Gln
            30                  35                  40

GAG CCC TTG ATG GTA CAG GCC AAT GCA GAT G GA CGG CCC CGG AGT CGG      315
Glu Pro Leu Met Val Gln Ala Asn Ala Asp G ly Arg Pro Arg Ser Arg
        45                  50                  55

CGA GCC CGG CAG TCA GAG GAG CAA GCC CCC C TG GTG GAG TCC TAC CTC      363
Arg Ala Arg Gln Ser Glu Glu Gln Ala Pro L eu Val Glu Ser Tyr Leu
60              65                  70                  75

AGC AGC AGT GGC AGC ACC AGC TAC CAA GTT C AA GAG GCC GAC TCG ATT      411
Ser Ser Ser Gly Ser Thr Ser Tyr Gln Val G ln Glu Ala Asp Ser Ile
                80                  85                  90

GCC AGT GTA CAG CTG GGA GCC ACC CGC CCA C CA GCA CCA GCT TCA GCC      459
Ala Ser Val Gln Leu Gly Ala Thr Arg Pro P ro Ala Pro Ala Ser Ala
            95                  100                 105

AAG AAA TCC AAG GGA GCG GCT GCA TCT GGG G GC CAG GGT GGA GCC CCT      507
Lys Lys Ser Lys Gly Ala Ala Ala Ser Gly G ly Gln Gly Gly Ala Pro
        110                 115                 120

AGG AAG GAG AAG AAG GGA AAG CAT AAA GGC A CC AGC GGG CCA GCA ACT      555
Arg Lys Glu Lys Lys Gly Lys His Lys Gly T hr Ser Gly Pro Ala Thr
125                 130                 135

CTG GCA GAA GAC AAG TCT GAG GCC CAA GGC C CA GTG CAG ATC TTG ACT      603
Leu Ala Glu Asp Lys Ser Glu Ala Gln Gly P ro Val Gln Ile Leu Thr
140                 145                 150                 155

GTG GGA CAG TCA GAC CAC GAC AAG GAT GCG G GA GAG ACA GCA GCC GGC      651
Val Gly Gln Ser Asp His Asp Lys Asp Ala G ly Glu Thr Ala Ala Gly
                160                 165                 170
```

```
GGG GGC GCA CAG CCC AGT GGG CAG GAC CTC C GT GCC ACG ATG CAG AGG      699
Gly Gly Ala Gln Pro Ser Gly Gln Asp Leu A rg Ala Thr Met Gln Arg
            175                 180                 185

AAG GGC ATC TCC AGC AGC ATG AGC TTT GAC G AG GAC GAG GAT GAG GAT      747
Lys Gly Ile Ser Ser Ser Met Ser Phe Asp G lu Asp Glu Asp Glu Asp
            190                 195                 200

GAA AAC AGC TCC AGC TCC TCC CAG CTA AAC A GC AAC ACC CGC CCT AGT      795
Glu Asn Ser Ser Ser Ser Ser Gln Leu Asn S er Asn Thr Arg Pro Ser
        205                 210                 215

TCT GCC ACT AGC AGA AAG TCC ATC CGG GAG G CA GCT TCA GCC CCC AGC      843
Ser Ala Thr Ser Arg Lys Ser Ile Arg Glu A la Ala Ser Ala Pro Ser
220                 225                 230                 235

CCA GCC GCC CCA GAG CCA CCA GTG GAT ATT G AG GTC CAG GAT CTA GAG      891
Pro Ala Ala Pro Glu Pro Pro Val Asp Ile G lu Val Gln Asp Leu Glu
                240                 245                 250

GAG TTT GCA CTG AGG CCA GCC CCA CAA GGG A TC ACC ATC AAA TGC CGC      939
Glu Phe Ala Leu Arg Pro Ala Pro Gln Gly I le Thr Ile Lys Cys Arg
            255                 260                 265

ATC ACT CGG GAC AAG AAG GGG ATG GAC CGC G GC ATG TAC CCC ACC TAC      987
Ile Thr Arg Asp Lys Lys Gly Met Asp Arg G ly Met Tyr Pro Thr Tyr
            270                 275                 280

TTT CTG CAC CTA GAC CGT GAG GAT GGC AAG A AG GTG TTC CTC CTG GCG     1035
Phe Leu His Leu Asp Arg Glu Asp Gly Lys L ys Val Phe Leu Leu Ala
        285                 290                 295

GGC AGG AAG AGA AAG AGT AAA ACT TCC AAT T AC CTC ATC TCT GTG GAC     1083
Gly Arg Lys Arg Lys Ser Lys Thr Ser Asn T yr Leu Ile Ser Val Asp
300                 305                 310                 315

CCA ACA GAC TTG TCT CGG GGA GGC GAT ACC T AT ATC GGG AAA TTG CGG     1131
Pro Thr Asp Leu Ser Arg Gly Gly Asp Thr T yr Ile Gly Lys Leu Arg
                320                 325                 330

TCC AAC CTG ATG GGC ACC AAG TTC ACC GTT T AT GAC AAT GGC GTC AAC     1179
Ser Asn Leu Met Gly Thr Lys Phe Thr Val T yr Asp Asn Gly Val Asn
            335                 340                 345

CCT CAG AAG GCA TCC TCT TCC ACG CTG GAA A GC GGA ACC TTG CGC CAG     1227
Pro Gln Lys Ala Ser Ser Ser Thr Leu Glu S er Gly Thr Leu Arg Gln
            350                 355                 360

GAG CTG GCA GCG GTG TGC TAT GAG ACA AAT G TC CTA GGC TTC AAG GGA     1275
Glu Leu Ala Ala Val Cys Tyr Glu Thr Asn V al Leu Gly Phe Lys Gly
            365                 370                 375

CCT CGG AAG ATG AGT GTG ATC GTC CCA GGC A TG AAC ATG GTT CAT GAG     1323
Pro Arg Lys Met Ser Val Ile Val Pro Gly M et Asn Met Val His Glu
380                 385                 390                 395

AGA GTC TGT ATC CGC CCC CGC AAT GAA CAT G AG ACC CTG TTA GCA CGC     1371
Arg Val Cys Ile Arg Pro Arg Asn Glu His G lu Thr Leu Leu Ala Arg
                400                 405                 410

TGG CAG AAC AAG AAC ACG GAG AGC ATC ATT G AG CTG CAG AAC AAG ACG     1419
Trp Gln Asn Lys Asn Thr Glu Ser Ile Ile G lu Leu Gln Asn Lys Thr
            415                 420                 425

CCA GTC TGG AAT GAT GAC ACA CAG TCC TAT G TA CTT AAC TTC CAC GGC     1467
Pro Val Trp Asn Asp Asp Thr Gln Ser Tyr V al Leu Asn Phe His Gly
            430                 435                 440

CGT GTC ACA CAG GCT TCT GTG AAG AAC TTC C AG ATC ATC CAC GGC AAT     1515
Arg Val Thr Gln Ala Ser Val Lys Asn Phe G ln Ile Ile His Gly Asn
            445                 450                 455

GAC CCG GAC TAC ATC GTC ATG CAG TTT GGC C GG GTA GCA GAA GAT GTG     1563
Asp Pro Asp Tyr Ile Val Met Gln Phe Gly A rg Val Ala Glu Asp Val
460                 465                 470                 475

TTC ACC ATG GAT TAC AAC TAC CCA CTG TGT G CA CTG CAG GCC TTC GCC     1611
Phe Thr Met Asp Tyr Asn Tyr Pro Leu Cys A la Leu Gln Ala Phe Ala
            480                 485                 490
```

```
ATT GCT CTG TCC AGC TTT GAC AGC AAG CTG G CC TGC GAG TAGAGGCCCC     1660
Ile Ala Leu Ser Ser Phe Asp Ser Lys Leu A la Cys Glu
            495                 500

CCACTGCCGT TAGGTGGCCC AGTCCGGAGT GGAGCTTGCC TGCCTGCCAA G ACAGGCCTG   1720

CCTACCCTCT GTTCATAGGC CCTCTATGGG CTTTCTGGTC TGACCAACCA G AGATTGGTT   1780

TGCTCTGCCT CTGCTGCTTG A                                              1801
```

(2) INFORMATION FOR SEQ ID NO:7:

(i) SEQUENCE CHARACTERISTICS:
        (A) LENGTH: 504 amino acids
        (B) TYPE: amino acid
        (D) TOPOLOGY: linear (ii) MOLECULE TYPE: protein (xi) SEQUENCE DESCRIPTION: SEQ ID NO:7:

```
Met Thr Ser Lys Pro His Ser Asp Trp Ile P ro Tyr Ser Val Leu Asp
 1               5                  10                 15

Asp Glu Gly Ser Asn Leu Arg Gln Gln Lys L eu Asp Arg Gln Arg Ala
            20                  25                  30

Leu Leu Glu Gln Lys Gln Lys Lys Arg G ln Glu Pro Leu Met Val
        35                  40                  45

Gln Ala Asn Ala Asp Gly Arg Pro Arg Ser A rg Arg Ala Arg Gln Ser
    50                  55                  60

Glu Glu Gln Ala Pro Leu Val Glu Ser Tyr L eu Ser Ser Ser Gly Ser
65                  70                  75                  80

Thr Ser Tyr Gln Val Gln Glu Ala Asp Ser I le Ala Ser Val Gln Leu
                85                  90                  95

Gly Ala Thr Arg Pro Pro Ala Pro Ala Ser A la Lys Lys Ser Lys Gly
            100                 105                 110

Ala Ala Ala Ser Gly Gly Gln Gly Gly Ala P ro Arg Lys Glu Lys Lys
        115                 120                 125

Gly Lys His Lys Gly Thr Ser Gly Pro Ala T hr Leu Ala Glu Asp Lys
    130                 135                 140

Ser Glu Ala Gln Gly Pro Val Gln Ile Leu T hr Val Gly Gln Ser Asp
145                 150                 155                 160

His Asp Lys Asp Ala Gly Glu Thr Ala Ala G ly Gly Gly Ala Gln Pro
                165                 170                 175

Ser Gly Gln Asp Leu Arg Ala Thr Met Gln A rg Lys Gly Ile Ser Ser
            180                 185                 190

Ser Met Ser Phe Asp Glu Asp Glu Asp Glu A sp Glu Asn Ser Ser Ser
        195                 200                 205

Ser Ser Gln Leu Asn Ser Asn Thr Arg Pro S er Ser Ala Thr Ser Arg
    210                 215                 220

Lys Ser Ile Arg Glu Ala Ala Ser Ala Pro S er Pro Ala Ala Pro Glu
225                 230                 235                 240

Pro Pro Val Asp Ile Glu Val Gln Asp Leu G lu Glu Phe Ala Leu Arg
                245                 250                 255

Pro Ala Pro Gln Gly Ile Thr Ile Lys Cys A rg Ile Thr Arg Asp Lys
            260                 265                 270

Lys Gly Met Asp Arg Gly Met Tyr Pro Thr T yr Phe Leu His Leu Asp
        275                 280                 285

Arg Glu Asp Gly Lys Lys Val Phe Leu Leu A la Gly Arg Lys Arg Lys
    290                 295                 300
```

```
Ser Lys Thr Ser Asn Tyr Leu Ile Ser Val A sp Pro Thr Asp Leu Ser
305                 310                 315                 320

Arg Gly Gly Asp Thr Tyr Ile Gly Lys Leu A rg Ser Asn Leu Met Gly
                325                 330                 335

Thr Lys Phe Thr Val Tyr Asp Asn Gly Val A sn Pro Gln Lys Ala Ser
                340                 345                 350

Ser Ser Thr Leu Glu Ser Gly Thr Leu Arg G ln Glu Leu Ala Ala Val
            355                 360                 365

Cys Tyr Glu Thr Asn Val Leu Gly Phe Lys G ly Pro Arg Lys Met Ser
        370                 375                 380

Val Ile Val Pro Gly Met Asn Met Val His G lu Arg Val Cys Ile Arg
385                 390                 395                 400

Pro Arg Asn Glu His Glu Thr Leu Leu Ala A rg Trp Gln Asn Lys Asn
                405                 410                 415

Thr Glu Ser Ile Ile Glu Leu Gln Asn Lys T hr Pro Val Trp Asn Asp
                420                 425                 430

Asp Thr Gln Ser Tyr Val Leu Asn Phe His G ly Arg Val Thr Gln Ala
                435                 440                 445

Ser Val Lys Asn Phe Gln Ile Ile His Gly A sn Asp Pro Asp Tyr Ile
            450                 455                 460

Val Met Gln Phe Gly Arg Val Ala Glu Asp V al Phe Thr Met Asp Tyr
465                 470                 475                 480

Asn Tyr Pro Leu Cys Ala Leu Gln Ala Phe A la Ile Ala Leu Ser Ser
                485                 490                 495

Phe Asp Ser Lys Leu Ala Cys Glu
                500
```

(2) INFORMATION FOR SEQ ID NO:8:

(i) SEQUENCE CHARACTERISTICS:
        (A) LENGTH: 1512 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1512

(xi) SEQUENCE DESCRIPTION: SEQ ID NO:8:

```
ATG ACT TCC AAG CCG CAT TCC GAC TGG ATT C CT TAC AGT GTC CTA GAT    48
Met Thr Ser Lys Pro His Ser Asp Trp Ile P ro Tyr Ser Val Leu Asp
1               5                   10                  15

GAT GAG GGC AGC AAC CTG AGG CAG CAG AAG C TC GAC CGG CAG CGG GCC    96
Asp Glu Gly Ser Asn Leu Arg Gln Gln Lys L eu Asp Arg Gln Arg Ala
            20                  25                  30

CTG TTG GAA CAG AAG CAG AAG AAG AAG CGC C AA GAG CCC TTG ATG GTA   144
Leu Leu Glu Gln Lys Gln Lys Lys Lys Arg G ln Glu Pro Leu Met Val
        35                  40                  45

CAG GCC AAT GCA GAT GGA CGG CCC CGG AGT C GG CGA GCC CGG CAG TCA   192
Gln Ala Asn Ala Asp Gly Arg Pro Arg Ser A rg Arg Ala Arg Gln Ser
    50                  55                  60

GAG GAG CAA GCC CCC CTG GTG GAG TCC TAC C TC AGC AGC AGT GGC AGC   240
Glu Glu Gln Ala Pro Leu Val Glu Ser Tyr L eu Ser Ser Ser Gly Ser
65                  70                  75                  80

ACC AGC TAC CAA GTT CAA GAG GCC GAC TCG A TT GCC AGT GTA CAG CTG   288
Thr Ser Tyr Gln Val Gln Glu Ala Asp Ser I le Ala Ser Val Gln Leu
                85                  90                  95
```

```
GGA GCC ACC CGC CCA CCA GCA CCA GCT TCA G CC AAG AAA TCC AAG GGA      336
Gly Ala Thr Arg Pro Pro Ala Pro Ala Ser A la Lys Lys Ser Lys Gly
            100             105                 110

GCG GCT GCA TCT GGG GGC CAG GGT GGA GCC C CT AGG AAG GAG AAG AAG      384
Ala Ala Ala Ser Gly Gly Gln Gly Gly Ala P ro Arg Lys Glu Lys Lys
                115             120                 125

GGA AAG CAT AAA GGC ACC AGC GGG CCA GCA A CT CTG GCA GAA GAC AAG      432
Gly Lys His Lys Gly Thr Ser Gly Pro Ala T hr Leu Ala Glu Asp Lys
        130             135                 140

TCT GAG GCC CAA GGC CCA GTG CAG ATC TTG A CT GTG GGA CAG TCA GAC      480
Ser Glu Ala Gln Gly Pro Val Gln Ile Leu T hr Val Gly Gln Ser Asp
145             150                 155                 160

CAC GAC AAG GAT GCG GGA GAG ACA GCA GCC G GC GGG GGC GCA CAG CCC      528
His Asp Lys Asp Ala Gly Glu Thr Ala Ala G ly Gly Gly Ala Gln Pro
                165                 170                 175

AGT GGG CAG GAC CTC CGT GCC ACG ATG CAG A GG AAG GGC ATC TCC AGC      576
Ser Gly Gln Asp Leu Arg Ala Thr Met Gln A rg Lys Gly Ile Ser Ser
            180                 185                 190

AGC ATG AGC TTT GAC GAG GAC GAG GAT GAG G AT GAA AAC AGC TCC AGC      624
Ser Met Ser Phe Asp Glu Asp Glu Asp Glu A sp Glu Asn Ser Ser Ser
                195             200                 205

TCC TCC CAG CTA AAC AGC AAC ACC CGC CCT A GT TCT GCC ACT AGC AGA      672
Ser Ser Gln Leu Asn Ser Asn Thr Arg Pro S er Ser Ala Thr Ser Arg
        210             215                 220

AAG TCC ATC CGG GAG GCA GCT TCA GCC CCC A GC CCA GCC GCC CCA GAG      720
Lys Ser Ile Arg Glu Ala Ala Ser Ala Pro S er Pro Ala Ala Pro Glu
225             230                 235                 240

CCA CCA GTG GAT ATT GAG GTC CAG GAT CTA G AG GAG TTT GCA CTG AGG      768
Pro Pro Val Asp Ile Glu Val Gln Asp Leu G lu Glu Phe Ala Leu Arg
                245             250                 255

CCA GCC CCA CAA GGG ATC ACC ATC AAA TGC C GC ATC ACT CGG GAC AAG      816
Pro Ala Pro Gln Gly Ile Thr Ile Lys Cys A rg Ile Thr Arg Asp Lys
            260             265                 270

AAG GGG ATG GAC CGC GGC ATG TAC CCC ACC T AC TTT CTG CAC CTA GAC      864
Lys Gly Met Asp Arg Gly Met Tyr Pro Thr T yr Phe Leu His Leu Asp
        275             280                 285

CGT GAG GAT GGC AAG AAG GTG TTC CTC CTG G CG GGC AGG AAG AGA AAG      912
Arg Glu Asp Gly Lys Lys Val Phe Leu Leu A la Gly Arg Lys Arg Lys
    290                 295                 300

AGT AAA ACT TCC AAT TAC CTC ATC TCT GTG G AC CCA ACA GAC TTG TCT      960
Ser Lys Thr Ser Asn Tyr Leu Ile Ser Val A sp Pro Thr Asp Leu Ser
305             310                 315                 320

CGG GGA GGC GAT ACC TAT ATC GGG AAA TTG C GG TCC AAC CTG ATG GGC     1008
Arg Gly Gly Asp Thr Tyr Ile Gly Lys Leu A rg Ser Asn Leu Met Gly
                325             330                 335

ACC AAG TTC ACC GTT TAT GAC AAT GGC GTC A AC CCT CAG AAG GCA TCC     1056
Thr Lys Phe Thr Val Tyr Asp Asn Gly Val A sn Pro Gln Lys Ala Ser
            340             345                 350

TCT TCC ACG CTG GAA AGC GGA ACC TTG CGC C AG GAG CTG GCA GCG GTG     1104
Ser Ser Thr Leu Glu Ser Gly Thr Leu Arg G ln Glu Leu Ala Ala Val
        355             360                 365

TGC TAT GAG ACA AAT GTC CTA GGC TTC AAG G GA CCT CGG AAG ATG AGT     1152
Cys Tyr Glu Thr Asn Val Leu Gly Phe Lys G ly Pro Arg Lys Met Ser
370             375                 380

GTG ATC GTC CCA GGC ATG AAC ATG GTT CAT G AG AGA GTC TGT ATC CGC     1200
Val Ile Val Pro Gly Met Asn Met Val His G lu Arg Val Cys Ile Arg
385             390                 395                 400

CCC CGC AAT GAA CAT GAG ACC CTG TTA GCA C GC TGG CAG AAC AAG AAC     1248
Pro Arg Asn Glu His Glu Thr Leu Leu Ala A rg Trp Gln Asn Lys Asn
                405             410                 415
```

```
ACG GAG AGC ATC ATT GAG CTG CAG AAC AAG A CG CCA GTC TGG AAT GAT     1296
Thr Glu Ser Ile Ile Glu Leu Gln Asn Lys T hr Pro Val Trp Asn Asp
            420                 425             430

GAC ACA CAG TCC TAT GTA CTT AAC TTC CAC G GC CGT GTC ACA CAG GCT     1344
Asp Thr Gln Ser Tyr Val Leu Asn Phe His G ly Arg Val Thr Gln Ala
            435                 440             445

TCT GTG AAG AAC TTC CAG ATC ATC CAC GGC A AT GAC CCG GAC TAC ATC     1392
Ser Val Lys Asn Phe Gln Ile Ile His Gly A sn Asp Pro Asp Tyr Ile
        450                 455             460

GTC ATG CAG TTT GGC CGG GTA GCA GAA GAT G TG TTC ACC ATG GAT TAC     1440
Val Met Gln Phe Gly Arg Val Ala Glu Asp V al Phe Thr Met Asp Tyr
465                 470             475                 480

AAC TAC CCA CTG TGT GCA CTG CAG GCC TTC G CC ATT GCT CTG TCC AGC     1488
Asn Tyr Pro Leu Cys Ala Leu Gln Ala Phe A la Ile Ala Leu Ser Ser
            485                 490             495

TTT GAC AGC AAG CTG GCC TGC GAG                                      1512
Phe Asp Ser Lys Leu Ala Cys Glu
            500
```

(2) INFORMATION FOR SEQ ID NO:9:

(i) SEQUENCE CHARACTERISTICS:
        (A) LENGTH: 2040 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 153..1671

(xi) SEQUENCE DESCRIPTION: SEQ ID NO:9:

```
TGGCGTGCAG CAGGGGCCTC GGCGGGGCCC AGCCCNCCGG TCCCGGGGAG G ATACGTCCC      60

GGGGGCGGCC CGGGAGCTGA GCAGGCCCCC CGCGCCGGCC CCTCCGGGCC C CGGCCTCCA     120

GAGCCGCAGC CACCGCCCCG CCCCCGAGAG AC ATG ACT TCC AA G CCG CAT TCC       173
                                   Met Thr Ser Lys Pro His Ser
                                    1               5

GAC TGG ATT CCC TAC AGT GTC TTA GAT GAT G AG GGC AGA AAC CTG AGG      221
Asp Trp Ile Pro Tyr Ser Val Leu Asp Asp G lu Gly Arg Asn Leu Arg
            10                  15              20

CAG CAG AAG CTT GAT CGG CAG CGG GCC CTG C TG GAG CAG AAG CAG AAG      269
Gln Gln Lys Leu Asp Arg Gln Arg Ala Leu L eu Glu Gln Lys Gln Lys
        25                  30              35

AAG AAG CGC CAG GAG CCC CTG ATG GTG CAG G CC AAT GCA GAT GGG CGG      317
Lys Lys Arg Gln Glu Pro Leu Met Val Gln A la Asn Ala Asp Gly Arg
40                  45              50                  55

CCC CGG AGC CGG CGG GCC CGG CAG TCA GAG G AA CAA GCC CCC CTG GTG      365
Pro Arg Ser Arg Arg Ala Arg Gln Ser Glu G lu Gln Ala Pro Leu Val
            60                  65              70

GAG TCC TAC CTC AGC AGC AGT GGC AGC ACC A GC TAC CAA GTT CAA GAG      413
Glu Ser Tyr Leu Ser Ser Ser Gly Ser Thr S er Tyr Gln Val Gln Glu
            75                  80              85

GCC GAC TCA CTC GCC AGT GTG CAG CTG GGA G CC ACG CGC CCA ACA GCA      461
Ala Asp Ser Leu Ala Ser Val Gln Leu Gly A la Thr Arg Pro Thr Ala
            90                  95              100

CCA GCT TCA GCC AAG AGA ACC AAG GCG GCA G CT ACA GCA GGG GGC CAG      509
Pro Ala Ser Ala Lys Arg Thr Lys Ala Ala A la Thr Ala Gly Gly Gln
        105                 110             115
```

```
GGT GGC GCC GCT AGG AAG GAG AAG AAG GGA A AG CAC AAA GGC ACC AGC       557
Gly Gly Ala Ala Arg Lys Glu Lys Lys Gly L ys His Lys Gly Thr Ser
120             125                 130                 135

GGG CCA GCA GCA CTG GCA GAA GAC AAG TCT G AG GCC CAA GGC CCA GTG       605
Gly Pro Ala Ala Leu Ala Glu Asp Lys Ser G lu Ala Gln Gly Pro Val
                140                 145                 150

CAG ATT CTG ACT GTG GGC CAG TCA GAC CAC G CC CAG GAC GCA GGG GAG       653
Gln Ile Leu Thr Val Gly Gln Ser Asp His A la Gln Asp Ala Gly Glu
            155                 160                 165

ACG GCA GCT GGT GGG GGC GAA CGG CCC AGC G GG CAG GAT CTC CGT GCC       701
Thr Ala Ala Gly Gly Gly Glu Arg Pro Ser G ly Gln Asp Leu Arg Ala
        170                 175                 180

ACG ATG CAG AGG AAG GGC ATC TCC AGC AGC A TG AGC TTT GAC GAG GAT       749
Thr Met Gln Arg Lys Gly Ile Ser Ser Ser M et Ser Phe Asp Glu Asp
    185                 190                 195

GAG GAG GAT GAG GAG GAG AAT AGC TCC AGC T CC TCC CAG CTA AAT AGT       797
Glu Glu Asp Glu Glu Glu Asn Ser Ser Ser S er Ser Gln Leu Asn Ser
200                 205                 210                 215

AAC ACC CGC CCC AGC TCT GCT ACT AGC AGG A AG TCC GTC AGG GAG GCA       845
Asn Thr Arg Pro Ser Ser Ala Thr Ser Arg L ys Ser Val Arg Glu Ala
                220                 225                 230

GCC TCA GCC CCT AGC CCA ACA GCT CCA GAG C AA CCA GTG GAC GTT GAG       893
Ala Ser Ala Pro Ser Pro Thr Ala Pro Glu G ln Pro Val Asp Val Glu
            235                 240                 245

GTC CAG GAT CTT GAG GAG TTT GCA CTG AGG C CG GCC CCC CAG GGT ATC       941
Val Gln Asp Leu Glu Glu Phe Ala Leu Arg P ro Ala Pro Gln Gly Ile
        250                 255                 260

ACC ATC AAA TGC CGC ATC ACT CGG GAC AAG A AA GGG ATG GAC CGG GGC       989
Thr Ile Lys Cys Arg Ile Thr Arg Asp Lys L ys Gly Met Asp Arg Gly
    265                 270                 275

ATG TAC CCC ACC TAC TTT CTG CAC CTG GAC C GT GAG GAT GGG AAG AAG      1037
Met Tyr Pro Thr Tyr Phe Leu His Leu Asp A rg Glu Asp Gly Lys Lys
280                 285                 290                 295

GTG TTC CTC CTG GCG GGA AGG AAG AGA AAG A AG AGT AAA ACT TCC AAT      1085
Val Phe Leu Leu Ala Gly Arg Lys Arg Lys L ys Ser Lys Thr Ser Asn
                300                 305                 310

TAC CTC ATC TCT GTG GAC CCA ACA GAC TTG T CT CGA GGA GGG GAC AGC      1133
Tyr Leu Ile Ser Val Asp Pro Thr Asp Leu S er Arg Gly Gly Asp Ser
            315                 320                 325

TAT ATC GGG AAA CTG CGG TCC AAC TTG ATG G GC ACC AAG TTC ACT GTT      1181
Tyr Ile Gly Lys Leu Arg Ser Asn Leu Met G ly Thr Lys Phe Thr Val
        330                 335                 340

TAT GAC AAT GGA GTC AAC CCT CAG AAG GCC T CA TCC TCC ACT TTG GAA      1229
Tyr Asp Asn Gly Val Asn Pro Gln Lys Ala S er Ser Ser Thr Leu Glu
    345                 350                 355

AGT GGA ACC TTA CGT CAG GAG CTG GCA GCT G TG TGC TAC GAG ACA AAC      1277
Ser Gly Thr Leu Arg Gln Glu Leu Ala Ala V al Cys Tyr Glu Thr Asn
360                 365                 370                 375

GTC TTA GGC TTC AAG GGG CCT CGG AAG ATG A GC GTG ATT GTC CCA GGC      1325
Val Leu Gly Phe Lys Gly Pro Arg Lys Met S er Val Ile Val Pro Gly
                380                 385                 390

ATG AAC ATG GTT CAT GAG AGA GTC TCT ATC C GC CCC CGC AAC GAG CAT      1373
Met Asn Met Val His Glu Arg Val Ser Ile A rg Pro Arg Asn Glu His
            395                 400                 405

GAG ACA CTG CTA GCA CGC TGG CAG AAT AAG A AC ACG GAG AGT ATC ATC      1421
Glu Thr Leu Leu Ala Arg Trp Gln Asn Lys A sn Thr Glu Ser Ile Ile
        410                 415                 420

GAG CTG CAA AAC AAG ACA CCT GTC TGG AAT G AT GAC ACA CAG TCC TAT      1469
Glu Leu Gln Asn Lys Thr Pro Val Trp Asn A sp Asp Thr Gln Ser Tyr
    425                 430                 435
```

```
GTA CTC AAC TTC CAT GGG CGC GTC ACA CAG G CC TCC GTG AAG AAC TTC        1517
Val Leu Asn Phe His Gly Arg Val Thr Gln A la Ser Val Lys Asn Phe
440                 445                 450                 455

CAG ATC ATC CAT GGC AAT GAC CCG GAC TAC A TC GTG ATG CAG TTT GGC        1565
Gln Ile Ile His Gly Asn Asp Pro Asp Tyr I le Val Met Gln Phe Gly
                460                 465                 470

CGG GTA GCA GAG GAT GTG TTC ACC ATG GAT T AC AAC TAC CCG CTG TGT        1613
Arg Val Ala Glu Asp Val Phe Thr Met Asp T yr Asn Tyr Pro Leu Cys
            475                 480                 485

GCA CTG CAG GCC TTT GCC ATT GCC CTG TCC A GC TTC GAC AGC AAG CTG        1661
Ala Leu Gln Ala Phe Ala Ile Ala Leu Ser S er Phe Asp Ser Lys Leu
        490                 495                 500

GCG TGC GAG T AGAGGCCTCT TCGTGCCCTT TGGGGTTGCC CAG CCTGGAG              1711
Ala Cys Glu
    505

CGGAGCTTGC CTGCCTGCCT GTGGAGACAG CCCTGCCTAT CCTCTGTATA T AGGCCTTCC      1771

GCCAGATGAA GCTTTGGCCC TCAGTGGGCT CCCTGGCCCA GCCAGCCAGG A ACTGGCTCC      1831

TTTGGCTCTG CTACTGAGGC AGGGGAGTAG TGGAGAGCGG GTGGGTGGGT G TTGAAGGGA      1891

TTGAGAATTA ATTCTTTCCA TGCCACGAGG ATCAACACAC ACTCCCACCC T TGGGTAGTA      1951

AGTGGTTGTT GTNAGTCGGT ACTTTACCAA AGCTTGAGCA ACCTCTTCCA A GCTTGGGAA      2011

AGGGCCGCAA AAAGGCATTA GGAGGGGAG                                         2040

(2) INFORMATION FOR SEQ ID NO:10:

(i) SEQUENCE CHARACTERISTICS:
         (A) LENGTH: 506 amino acids
         (B) TYPE: amino acid
         (D) TOPOLOGY: linear (ii) MOLECULE TYPE: protein (xi) SEQUENCE DESCRIPTION: SEQ ID NO:10:

Met Thr Ser Lys Pro His Ser Asp Trp Ile P ro Tyr Ser Val Leu Asp
 1               5                  10                  15

Asp Glu Gly Arg Asn Leu Arg Gln Gln Lys L eu Asp Arg Gln Arg Ala
            20                  25                  30

Leu Leu Glu Gln Lys Gln Lys Lys Arg G ln Glu Pro Leu Met Val
        35                  40                  45

Gln Ala Asn Ala Asp Gly Arg Pro Arg Ser A rg Arg Ala Arg Gln Ser
    50                  55                  60

Glu Glu Gln Ala Pro Leu Val Glu Ser Tyr L eu Ser Ser Gly Ser
65                  70                  75                  80

Thr Ser Tyr Gln Val Gln Glu Ala Asp Ser L eu Ala Ser Val Gln Leu
                85                  90                  95

Gly Ala Thr Arg Pro Thr Ala Pro Ala Ser A la Lys Arg Thr Lys Ala
            100                 105                 110

Ala Ala Thr Ala Gly Gly Gln Gly Gly Ala A la Arg Lys Glu Lys Lys
        115                 120                 125

Gly Lys His Lys Gly Thr Ser Gly Pro Ala A la Leu Ala Glu Asp Lys
    130                 135                 140

Ser Glu Ala Gln Gly Pro Val Gln Ile Leu T hr Val Gly Gln Ser Asp
145                 150                 155                 160

His Ala Gln Asp Ala Gly Glu Thr Ala Ala G ly Gly Gly Glu Arg Pro
                165                 170                 175

Ser Gly Gln Asp Leu Arg Ala Thr Met Gln A rg Lys Gly Ile Ser Ser
            180                 185                 190
```

```
Ser Met Ser Phe Asp Glu Asp Glu Asp Glu Glu Asn Ser Ser
    195                 200             205

Ser Ser Ser Gln Leu Asn Ser Asn Thr Arg Pro Ser Ser Ala Thr Ser
    210                 215             220

Arg Lys Ser Val Arg Glu Ala Ser Ala Pro Ser Pro Thr Ala Pro
225             230             235             240

Glu Gln Pro Val Asp Val Glu Val Gln Asp Leu Glu Glu Phe Ala Leu
            245             250             255

Arg Pro Ala Pro Gln Gly Ile Thr Ile Lys Cys Arg Ile Thr Arg Asp
            260             265             270

Lys Lys Gly Met Asp Arg Gly Met Tyr Pro Thr Tyr Phe Leu His Leu
            275             280             285

Asp Arg Glu Asp Gly Lys Lys Val Phe Leu Leu Ala Gly Arg Lys Arg
290             295             300

Lys Lys Ser Lys Thr Ser Asn Tyr Leu Ile Ser Val Asp Pro Thr Asp
305             310             315             320

Leu Ser Arg Gly Gly Asp Ser Tyr Ile Gly Lys Leu Arg Ser Asn Leu
            325             330             335

Met Gly Thr Lys Phe Thr Val Tyr Asp Asn Gly Val Asn Pro Gln Lys
            340             345             350

Ala Ser Ser Ser Thr Leu Glu Ser Gly Thr Leu Arg Gln Glu Leu Ala
            355             360             365

Ala Val Cys Tyr Glu Thr Asn Val Leu Gly Phe Lys Gly Pro Arg Lys
            370             375             380

Met Ser Val Ile Val Pro Gly Met Asn Met Val His Glu Arg Val Ser
385             390             395             400

Ile Arg Pro Arg Asn Glu His Glu Thr Leu Leu Ala Arg Trp Gln Asn
            405             410             415

Lys Asn Thr Glu Ser Ile Ile Glu Leu Gln Asn Lys Thr Pro Val Trp
            420             425             430

Asn Asp Asp Thr Gln Ser Tyr Val Leu Asn Phe His Gly Arg Val Thr
            435             440             445

Gln Ala Ser Val Lys Asn Phe Gln Ile Ile His Gly Asn Asp Pro Asp
450             455             460

Tyr Ile Val Met Gln Phe Gly Arg Val Ala Glu Asp Val Phe Thr Met
465             470             475             480

Asp Tyr Asn Tyr Pro Leu Cys Ala Leu Gln Ala Phe Ala Ile Ala Leu
            485             490             495

Ser Ser Phe Asp Ser Lys Leu Ala Cys Glu
            500             505
```

(2) INFORMATION FOR SEQ ID NO:11:

(i) SEQUENCE CHARACTERISTICS:
        (A) LENGTH: 1518 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1518

(xi) SEQUENCE DESCRIPTION: SEQ ID NO:11:

```
ATG ACT TCC AAG CCG CAT TCC GAC TGG ATT C CC TAC AGT GTC TTA GAT      48
Met Thr Ser Lys Pro His Ser Asp Trp Ile P ro Tyr Ser Val Leu Asp
 1               5                  10                  15

GAT GAG GGC AGA AAC CTG AGG CAG CAG AAG C TT GAT CGG CAG CGG GCC      96
Asp Glu Gly Arg Asn Leu Arg Gln Gln Lys L eu Asp Arg Gln Arg Ala
                 20                  25                  30

CTG CTG GAG CAG AAG CAG AAG AAG AAG CGC C AG GAG CCC CTG ATG GTG     144
Leu Leu Glu Gln Lys Gln Lys Lys Lys Arg G ln Glu Pro Leu Met Val
             35                  40                  45

CAG GCC AAT GCA GAT GGG CGG CCC CGG AGC C GG CGG GCC CGG CAG TCA     192
Gln Ala Asn Ala Asp Gly Arg Pro Arg Ser A rg Arg Ala Arg Gln Ser
         50                  55                  60

GAG GAA CAA GCC CCC CTG GTG GAG TCC TAC C TC AGC AGC AGT GGC AGC     240
Glu Glu Gln Ala Pro Leu Val Glu Ser Tyr L eu Ser Ser Ser Gly Ser
 65                  70                  75                  80

ACC AGC TAC CAA GTT CAA GAG GCC GAC TCA C TC GCC AGT GTG CAG CTG     288
Thr Ser Tyr Gln Val Gln Glu Ala Asp Ser L eu Ala Ser Val Gln Leu
                 85                  90                  95

GGA GCC ACG CGC CCA ACA GCA CCA GCT TCA G CC AAG AGA ACC AAG GCG     336
Gly Ala Thr Arg Pro Thr Ala Pro Ala Ser A la Lys Arg Thr Lys Ala
             100                 105                 110

GCA GCT ACA GCA GGG GGC CAG GGT GGC GCC G CT AGG AAG GAG AAG AAG     384
Ala Ala Thr Ala Gly Gly Gln Gly Gly Ala A la Arg Lys Glu Lys Lys
         115                 120                 125

GGA AAG CAC AAA GGC ACC AGC GGG CCA GCA G CA CTG GCA GAA GAC AAG     432
Gly Lys His Lys Gly Thr Ser Gly Pro Ala A la Leu Ala Glu Asp Lys
 130                 135                 140

TCT GAG GCC CAA GGC CCA GTG CAG ATT CTG A CT GTG GGC CAG TCA GAC     480
Ser Glu Ala Gln Gly Pro Val Gln Ile Leu T hr Val Gly Gln Ser Asp
145                 150                 155                 160

CAC GCC CAG GAC GCA GGG GAG ACG GCA GCT G GT GGG GGC GAA CGG CCC     528
His Ala Gln Asp Ala Gly Glu Thr Ala Ala G ly Gly Gly Glu Arg Pro
                 165                 170                 175

AGC GGG CAG GAT CTC CGT GCC ACG ATG CAG A GG AAG GGC ATC TCC AGC     576
Ser Gly Gln Asp Leu Arg Ala Thr Met Gln A rg Lys Gly Ile Ser Ser
             180                 185                 190

AGC ATG AGC TTT GAC GAG GAT GAG GAG GAT G AG GAG GAG AAT AGC TCC     624
Ser Met Ser Phe Asp Glu Asp Glu Glu Asp G lu Glu Glu Asn Ser Ser
         195                 200                 205

AGC TCC TCC CAG CTA AAT AGT AAC ACC CGC C CC AGC TCT GCT ACT AGC     672
Ser Ser Ser Gln Leu Asn Ser Asn Thr Arg P ro Ser Ser Ala Thr Ser
 210                 215                 220

AGG AAG TCC GTC AGG GAG GCA GCC TCA GCC C CT AGC CCA ACA GCT CCA     720
Arg Lys Ser Val Arg Glu Ala Ala Ser Ala P ro Ser Pro Thr Ala Pro
225                 230                 235                 240

GAG CAA CCA GTG GAC GTT GAG GTC CAG GAT C TT GAG GAG TTT GCA CTG     768
Glu Gln Pro Val Asp Val Glu Val Gln Asp L eu Glu Glu Phe Ala Leu
                 245                 250                 255

AGG CCG GCC CCC CAG GGT ATC ACC ATC AAA T GC CGC ATC ACT CGG GAC     816
Arg Pro Ala Pro Gln Gly Ile Thr Ile Lys C ys Arg Ile Thr Arg Asp
             260                 265                 270

AAG AAA GGG ATG GAC CGG GGC ATG TAC CCC A CC TAC TTT CTG CAC CTG     864
Lys Lys Gly Met Asp Arg Gly Met Tyr Pro T hr Tyr Phe Leu His Leu
         275                 280                 285

GAC CGT GAG GAT GGG AAG AAG GTG TTC CTC C TG GCG GGA AGG AAG AGA     912
Asp Arg Glu Asp Gly Lys Lys Val Phe Leu L eu Ala Gly Arg Lys Arg
 290                 295                 300
```

```
AAG AAG AGT AAA ACT TCC AAT TAC CTC ATC T CT GTG GAC CCA ACA GAC      960
Lys Lys Ser Lys Thr Ser Asn Tyr Leu Ile S er Val Asp Pro Thr Asp
305                 310                 315                 320

TTG TCT CGA GGA GGG GAC AGC TAT ATC GGG A AA CTG CGG TCC AAC TTG     1008
Leu Ser Arg Gly Gly Asp Ser Tyr Ile Gly L ys Leu Arg Ser Asn Leu
            325                 330                 335

ATG GGC ACC AAG TTC ACT GTT TAT GAC AAT G GA GTC AAC CCT CAG AAG     1056
Met Gly Thr Lys Phe Thr Val Tyr Asp Asn G ly Val Asn Pro Gln Lys
                340                 345                 350

GCC TCA TCC TCC ACT TTG GAA AGT GGA ACC T TA CGT CAG GAG CTG GCA     1104
Ala Ser Ser Ser Thr Leu Glu Ser Gly Thr L eu Arg Gln Glu Leu Ala
        355                 360                 365

GCT GTG TGC TAC GAG ACA AAC GTC TTA GGC T TC AAG GGG CCT CGG AAG     1152
Ala Val Cys Tyr Glu Thr Asn Val Leu Gly P he Lys Gly Pro Arg Lys
            370                 375                 380

ATG AGC GTG ATT GTC CCA GGC ATG AAC ATG G TT CAT GAG AGA GTC TCT     1200
Met Ser Val Ile Val Pro Gly Met Asn Met V al His Glu Arg Val Ser
385                 390                 395                 400

ATC CGC CCC CGC AAC GAG CAT GAG ACA CTG C TA GCA CGC TGG CAG AAT     1248
Ile Arg Pro Arg Asn Glu His Glu Thr Leu L eu Ala Arg Trp Gln Asn
            405                 410                 415

AAG AAC ACG GAG AGT ATC ATC GAG CTG CAA A AC AAG ACA CCT GTC TGG     1296
Lys Asn Thr Glu Ser Ile Ile Glu Leu Gln A sn Lys Thr Pro Val Trp
                420                 425                 430

AAT GAT GAC ACA CAG TCC TAT GTA CTC AAC T TC CAT GGG CGC GTC ACA     1344
Asn Asp Asp Thr Gln Ser Tyr Val Leu Asn P he His Gly Arg Val Thr
        435                 440                 445

CAG GCC TCC GTG AAG AAC TTC CAG ATC ATC C AT GGC AAT GAC CCG GAC     1392
Gln Ala Ser Val Lys Asn Phe Gln Ile Ile H is Gly Asn Asp Pro Asp
    450                 455                 460

TAC ATC GTG ATG CAG TTT GGC CGG GTA GCA G AG GAT GTG TTC ACC ATG     1440
Tyr Ile Val Met Gln Phe Gly Arg Val Ala G lu Asp Val Phe Thr Met
465                 470                 475                 480

GAT TAC AAC TAC CCG CTG TGT GCA CTG CAG G CC TTT GCC ATT GCC CTG     1488
Asp Tyr Asn Tyr Pro Leu Cys Ala Leu Gln A la Phe Ala Ile Ala Leu
            485                 490                 495

TCC AGC TTC GAC AGC AAG CTG GCG TGC GAG                              1518
Ser Ser Phe Asp Ser Lys Leu Ala Cys Glu
                500                 505

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CGTGGAGGTG GACGAACC                                                    18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

```
    (ii) MOLECULE TYPE: cDNA (xi) SEQUENCE DESCRIPTION: SEQ ID NO:13:

CCGTGTCCAG GTGCAGGA                                                    18
```